US008263755B2

(12) United States Patent
Findeis

(10) Patent No.: US 8,263,755 B2
(45) Date of Patent: Sep. 11, 2012

(54) SYNTHESIS OF COMPOUNDS USEFUL AS MODULATORS OF AMYLOID-BETA PRODUCTION

(75) Inventor: Mark A. Findeis, Belmont, MA (US)

(73) Assignee: Satori Pharmaceuticals, Inc., Cambridge, MA (US)

(*) Notice: Subject to any disclaimer, the term of this patent is extended or adjusted under 35 U.S.C. 154(b) by 391 days.

(21) Appl. No.: 12/515,703

(22) PCT Filed: Nov. 20, 2007

(86) PCT No.: PCT/US2007/085161
§ 371 (c)(1),
(2), (4) Date: Jan. 17, 2010

(87) PCT Pub. No.: WO2008/136863
PCT Pub. Date: Nov. 13, 2008

(65) Prior Publication Data
US 2010/0197615 A1 Aug. 5, 2010

Related U.S. Application Data

(60) Provisional application No. 60/860,185, filed on Nov. 20, 2006.

(51) Int. Cl.
C07G 3/00 (2006.01)
C07H 17/00 (2006.01)
A01N 45/00 (2006.01)
(52) U.S. Cl. .................................... 536/18.5; 514/26
(58) Field of Classification Search .......................... None
See application file for complete search history.

(56) References Cited

U.S. PATENT DOCUMENTS

| 3,160,626 | A | 12/1964 | Oxley |
| 4,650,750 | A | 3/1987 | Giese et al. |
| 4,709,016 | A | 11/1987 | Giese et al. |
| 5,360,819 | A | 11/1994 | Giese et al. |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 5,958,770 | A | 9/1999 | Cham et al. |
| 6,649,196 | B2 | 11/2003 | Eckman et al. |
| 7,300,677 | B2 | 11/2007 | Eckman et al. |
| 7,851,641 | B2 | 12/2010 | Findeis et al. |
| 2003/0060425 | A1 | 3/2003 | Ahlem et al. |
| 2004/0220115 | A1 | 11/2004 | Cham |
| 2007/0149491 | A1 | 6/2007 | Findeis |
| 2008/0299229 | A1 | 12/2008 | Eckman et al. |
| 2010/0056487 | A1 | 3/2010 | Findeis et al. |
| 2010/0144689 | A1 | 6/2010 | Findeis et al. |
| 2011/0136749 | A1 | 6/2011 | Findeis et al. |
| 2011/0136750 | A1 | 6/2011 | Findeis et al. |

FOREIGN PATENT DOCUMENTS

| JP | 59020298 | 2/1984 |
| JP | 09030977 | 2/1997 |
| KR | 9300059 | 1/1993 |
| WO | WO01/23407 A1 | 4/2001 |
| WO | WO0203803 | 1/2002 |
| WO | WO2004/091484 | 10/2004 |
| WO | WO2006/037016 | 4/2006 |

OTHER PUBLICATIONS

"Black Cohosh" The ABC Clinical Guide to Herbs, pp. 13-22, 2003 by the American Botanical Council (ABC).
Chromadex listing of phytochemical standards.
International Search Report and Written Opinion for PCT/US06/19014 published as WO2006/124956 on Nov. 23, 2006.
International Search Report and Written Opinion for PCT/US06/44880 published as WO2008/063165 on May 29, 2008.
International Search Report and Written Opinion for PCT/US07/85161 published as WO2008/136863 on Nov. 13, 2008.
International Search Report and Written Opinion for PCT/US07/85229 published as WO2008/130449 on Oct. 30, 2008.
Kusano, et al., "Studies on the Constituents of Cimiciguga Species. XVIII. Four New Xylosides from the Aerial Parts of Cimicifuga simplex Wormsk," Chem. Pharm. Bull., 1996, 44(1): 167-172.
Takahara, et al., "Antimalarial Activity and Nucleoside Transport Inhibitory Activity of the Triterpenic Constituents of Cimicifuga spp." Biol. Pharm. Bull., 1998, 21(8): 823-828.
Yager, et al., "Natural Product Extracts that Reduce Accumulation of the Alzheimer's Amyloid B-Peptide" Journal of Molecular Neuroscience, 2002, 19: 129-133.
Gouras, et al., "Testosterone reduces neuronal secretion of Alzheimer's beta amyloid peptides" Proceedings of National Academy of Sciences of the United States, 2000, 97(3): 1202-1205.
Nowak et al., "Niobium Compounds: Preparation, Characterization, and Application in Heterogeneous Catalysis," Chem. Rev., 1999, 99(12): 1-23.
Selkoe, "Alzheimer's Disease: Genes, Proteins, and Therapy," Physiological Reviews, 2001, 81(2): 741-766.
Younkin, "The Role of Aβ42 in Alzheimer's Disease," J. Physiol. Paris., 1998, 92: 289-92.
Parvathy et al., "Correlation Between Abx-40-, Abx-42-, and Abx-43-Containing Amyoid Plaques and Cognitive Decline" Arch Neurol., 2001, 58: 2025-32.
Ishii, et al., "Increased Ab 42(43)-Plaque Deposition in Early-Onset Familial Alzheimer's Disease Brains with the Deletion of Exon 9 and the Missense Point Mutation (H163R) in the PS-1 Gene," Neuroscience Letters, 1997, 228: 17-20.
Kosaka, et al., "The βAPP717 Alzheimer Mutation Increases the Percentage of Plasma Amyloid-β Protein Ending at Aβ42(43)," Neurology, 1997, 48: 741-745.

(Continued)

Primary Examiner — Layla Bland
(74) Attorney, Agent, or Firm — Choate, Hall & Stewart LLP; Andrea L. C. Robidoux; Danielle M. Nihan

(57) ABSTRACT

As described herein, the present invention provides methods for preparing compounds useful for treating or lessening the severity of a neurodegenerative disorder. The present invention also provides methods of treating or lessening the severity of such disorders wherein said method comprises administering to a patient a compound of the present invention, or composition thereof. Said method is useful for treating or lessening the severity of, for example, Alzheimer's disease.

15 Claims, No Drawings

OTHER PUBLICATIONS

Mann, et al., "Predominant Deposition of Amyloid-1342(43) in Plaques in Cases of Alzheimer's Disease and Hereditary Cerebral Hemorrhage Associated with Mutations in the Amyloid Precursor Protein Gene" Am. J. Pathol., 1996, 148: 1257-1266.

Gravina, et al. "Amyloid β Protein (Aβ) in Alzheimer's Disease Brain," J. Biol. Chem., 1995, 270: 7013-7016.

Iwatsubo, et al., "Full-Length Amyloid-β(1-42(43)) and Amino-Terminally Modified and Truncated Amyloid-β42(43) Deposit in Diffuse Plaques," Am. J. Pathol., 1996, 149: 1823-30.

Roher, et al., "β-Amyloid-(1-42) is a Major Component of Cerebrovascular Amyloid Deposits: Implications for the Pathology of Alzheimer Disease," Proc. Natl. Acad. Sci. USA., 1993, 90: 10836-10840.

Tamaoka, et al. "Biochemical Evidence for the Long-Tail form (A beta 1-42/43) of Amyloid beta Protein as a Seed Molecule in Cerebral Deposits of Alzheimer's Disease," Biochem. Biophys. Res. Commun., 1994, 205: 834-42.

Rockenstein, et al., "Early Formation of Mature Amyloid-β Protein Deposits in a Mutant APP Transgenic Model Depends on Levels of Aβ1-42," J. Neurosci. Res., 2001, 66: 573-582.

Terai, et al. "β-Amyloid Deposits in Transgenic Mice Expressing Human β-Amyloid Precursor Protein have the Same Characteristics as Those in Alzheimer's Disease," Neuroscience, 2001, 104: 299-310.

Iwatsubo, et al., "Amyloid β Protein (Aβ) Deposition: Aβ42(43) Precedes Aβ40 in Down Syndrome," Ann. Neurol., 1995, 37: 294-299.

Berge, et al., "Pharmaceutical Salts," J. Pharmaceutical Sciences, 1977, 66: 1-19.

Gaiano, et al., "The Role of Notch in Promoting Glial and Neural Stem Cell Fates," Annu. Rev. Neurosci., 2002, 25: 471-490.

Lleo, et al., "Notch1 Competes with the Amyloid Precursor Protein for γ-Secretase and Down-regulates Presenilin-1 Gene Expression," The Journal of Biological Chemistry, 2003, 48: 47370-47375.

Minter, et al., "Inhibitors of γ-secretase block in vivo and in vitro T helper type 1 polarization by preventing Notch upregulation of Tbx21," Nature Immunology, 2005, 6(7): 680-688.

Wong, et al., "Chronic Treatment with the γ-Secretase Inhibitor LY-411,575 Inhibits B-Amyloid Peptide Production and Alters Lymphopoiesis and Intestinal Cell Differentiation," The Journal of Biological Chemistry, 2004, 279(26): 12876-12882.

Milano et al., "Modulation of Notch Processing by γ-Secretase Inhibitors Causes Intestinal Goblet Cell Metaplasia and Induction of Genes Known to Specify Gut Secretory Lineage Differentiation," Toxicological Sciences, 2004, 82: 341-358.

Wang, et al., "The Profile of Soluble Amyloid β Protein in Cultured Cell Media," The Journal of Biological Chemistry, 1996, 50: 31894-31902.

He, et al., "Cimicifuga species identification by high performance liquid chromatography-photodiode array/mass spectrometric/evaporative light scattering detection for quality control of black cohosh products," J. Chromatogr, 2006, 1112(1): 241-254.

Zhang, et al., "Cycloartane Glycosides from Cimicifuga dahurica," Chemical Pham. Bull. 2001, 49(11): 1468-1470.

Kamernitskii et al., "Transformed steroids 91. Heterocyclization of 23-Substituted 16 alpha, 17 alpha-Epoxy-20-Keto steroids," Russian Chemical Bulletin, 1978, 27(1): 160-164. Abstract.

Supplementary European Search Report for PCT/US07/85229 published as EP 07874499 on Feb. 22, 2010.

Wrzeciono, et al., "Syntheses de Triterpenes Tetracycliques Marques (+). I.—Lanosterol, Cycloartenol, Parkeol et 31-Norcycloartenol (14C-25) Ou (D6-26/27). II.—Lanosterol et Cycloartenol (T-2)," Bulletin de la Societe Chimique de France, 1970, 3:966-974.

De Pascual, et al., "Triterpenes from Euphorbia broteri," Phytochemistry, 1987, 26(6): 1767-1776.

Bruttomesso, et al., "Mechanistic Studies of the Rearrangements of Steroidal 16,17-Ketols and Syntheses of 20→16-cis-γ-Carbolactones," Bioorganic & Medicinal Chemistry, 1999, 7: 943-947.

Singh, et al., "Partial Synthesis from Cycloartenol, Cyclolaudenol Part 1: Mangiferolic Acid, Ambolic Acid[b,c]," Tetrahedron, 1977, 33: 817-819.

Della Greca, et al., "Cycloartane Triterpenes from Juncus effusus," Phytochemistry, 1994, 35(4): 1017-1022.

Schumacher et al., "Steroid hormones and neurosteroids in normal and pathological aging of the nervous system," Progress in Neurobiology, 2003, 71: 3-29.

De Vivar, A. et al., "Triterpenes in Parthenium argentatum, structures of argtntatins C and D." Phytochemistry, Pergamon Press, GB, vol. 29, No. 3, Jan. 1, 1990.

Ganenko, T. V. et al., "Triterpenoids of Thalictrum foetidum and their biological activity." Proceedings of the FCES Third International Conference on Chemistry and Biotechnology of Biologically Active Natural Products, 1985, pp. 330-335.

Herz, W. et al., "Cycloartanes form Lindheimera texana." Phytochemistry, vol. 24, No. 11, 1985, pp. 2645-2654.

Kusano, A. et al., "Studies on the Constituents of Cimicifuga Species. XIX. Eight New Glycosides from Cimicifuga simplex WORMSK." Chemical & Pharmaceutical Bulletin, vol. 44, No. 11, 1996, pp. 2078-2085.

Sakurai, N. et al., "Cancer preventive agents. Part 1: Chemopreventive potential of cimigenol, cimigelnol-3,15-dione, and related compounds." Bioorganic & Medicinal Chemistry, Pergamon, GB, vol. 13, No. 4, Feb. 15, 2005.

Sakurai, N. et al., "Studies on the Chinese Crude Drug "Shoma." V. Structures of 24-0-Hydroxycimigenol Xyloside." Chemical & Pharmaceutical Bulletin, vol. 29, No. 4, 1981, pp. 955-960.

Supplementary Partial European Search Report, EP 06 83 8050, published on Jul. 1, 2009 under EP 2073637, mailed on Nov. 30, 2011.

SYNTHESIS OF COMPOUNDS USEFUL AS MODULATORS OF AMYLOID-BETA PRODUCTION

CROSS-REFERENCE TO RELATED APPLICATIONS

This application is a U.S. national phase application under 35 U.S.C. §371 of international PCT application number PCT/US2007/085161, filed Nov. 20, 2007, which claims priority to U.S. provisional application Ser. No. 60/860,185, filed Nov. 20, 2006, the entirety of each of which is hereby incorporated by reference.

FIELD OF THE INVENTION

The present invention relates to compounds that modulate amyloid-beta peptide production, processes for their preparation, and uses thereof.

BACKGROUND OF THE INVENTION

The central role of the long form of amyloid beta-peptide, in particular Aβ(1-42), in Alzheimer's disease has been established through a variety of histopathological, genetic and biochemical studies. See Selkoe, D J, *Physiol. Rev.* 2001, 81:741-766, Alzheimer's disease: genes, proteins, and therapy, and Younkin S G, *J Physiol Paris.* 1998, 92:289-92, The role of A beta 42 in Alzheimer's disease. Specifically, it has been found that deposition in the brain of Aβ(1-42) is an early and invariant feature of all forms of Alzheimer's disease. In fact, this occurs before a diagnosis of Alzheimer's disease is possible and before the deposition of the shorter primary form of A-beta, Aβ(1-40). See Parvathy S, et al. *Arch Neurol.* 2001, 58:2025-32, Correlation between Abetax-40-, Abetax-42-, and Abetax-43-containing amyloid plaques and cognitive decline. Further implication of Aβ(1-42) in disease etiology comes from the observation that mutations in presenilin (gamma secretase) genes associated with early onset familial forms of Alzheimer's disease uniformly result in increased levels of Aβ(1-42). See Ishii K, et al. *Neurosci Lett.* 1997, 228:17-20, Increased A beta 42(43)-plaque deposition in early-onset familial Alzheimer's disease brains with the deletion of exon 9 and the missense point mutation (H163R) in the PS-1 gene. Additional mutations in the amyloid precursor protein APP raise total Aβ and in some cases raise Aβ(1-42) alone. See Kosaka T, et al. *Neurology,* 48:741-5, The beta APP717 Alzheimer mutation increases the percentage of plasma amyloid-beta protein ending at A beta42(43). Although the various APP mutations may influence the type, quantity, and location of Aβ deposited, it has been found that the predominant and initial species deposited in the brain parenchyma is long Aβ (Mann). See Mann D M, et al. *Am J Pathol.* 1996, 148:1257-66, Predominant deposition of amyloid-beta 42(43) in plaques in cases of Alzheimer's disease and hereditary cerebral hemorrhage associated with mutations in the amyloid precursor protein gene.

In early deposits of Aβ, when most deposited protein is in the form of amorphous or diffuse plaques, virtually all of the Aβ is of the long form. See Gravina S A, et al. *J Biol Chem,* 270:7013-6, Amyloid beta protein (A beta) in Alzheimer's disease brain. Biochemical and immunocytochemical analysis with antibodies specific for forms ending at A beta 40 or A beta 42(43); Iwatsubo T, et al. *Am J Pathol.* 1996, 149:1823-30, Full-length amyloid-beta (1-42(43)) and amino-terminally modified and truncated amyloid-beta 42(43) deposit in diffuse plaques; and Roher A E, et al. *Proc Natl Acad Sci USA.* 1993, 90:10836-40, beta-Amyloid-(1-42) is a major component of cerebrovascular amyloid deposits: implications for the pathology of Alzheimer disease. These initial deposits of Aβ(1-42) then are able to seed the further deposition of both long and short forms of Aβ. See Tamaoka A, et al. *Biochem Biophys Res Commun.* 1994, 205:834-42, Biochemical evidence for the long-tail form (A beta 1-42/43) of amyloid beta protein as a seed molecule in cerebral deposits of Alzheimer's disease.

In transgenic animals expressing Aβ, deposits were associated with elevated levels of Aβ(1-42), and the pattern of deposition is similar to that seen in human disease with Aβ(1-42) being deposited early followed by deposition of Aβ(1-40). See Rockenstein E, et al. *J Neurosci Res.* 2001, 66:573-82, Early formation of mature amyloid-beta protein deposits in a mutant APP transgenic model depends on levels of Abeta (1-42); and Terai K, et al. *Neuroscience* 2001, 104:299-310, beta-Amyloid deposits in transgenic mice expressing human beta-amyloid precursor protein have the same characteristics as those in Alzheimer's disease. Similar patterns and timing of deposition are seen in Down's Syndrome patients in which Aβ expression is elevated and deposition is accelerated. See Iwatsubo T, et al. *Ann Neurol.* 1995, 37:294-9, Amyloid beta protein (A beta) deposition: A beta 42(43) precedes A beta 40 in Down syndrome.

Accordingly, selective lowering of Aβ(1-42) thus emerges as a disease-specific strategy for reducing the amyloid forming potential of all forms of Aβ, slowing or stopping the formation of new deposits of Aβ, inhibiting the formation of soluble toxic oligomers of Aβ, and thereby slowing or halting the progression of neurodegeneration.

SUMMARY OF THE INVENTION

As described herein, the present invention provides methods for preparing compounds useful as modulators of amyloid-beta production. Such compounds are useful for treating or lessening the severity of a neurodegenerative disorder. The present invention also provides intermediates useful in carrying out such synthetic methods.

DETAILED DESCRIPTION OF CERTAIN EMBODIMENTS OF THE INVENTION

1. General Description of Compounds of the Invention

Methods and intermediates of the present invention are useful for preparing compounds as described in, e.g. U.S. patent application Ser. No. 11/434,726, filed May 16, 2006, published as US 20070010503, in the name of Findeis et al., the entirety of which is incorporated herein by reference. In certain embodiments, the present compounds are generally prepared according to Scheme I set forth below:

Scheme I:

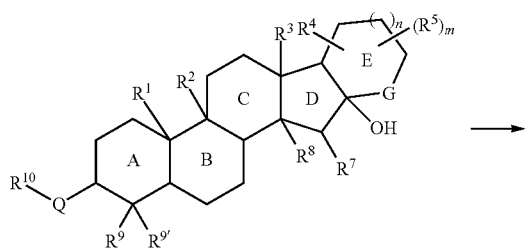

-continued

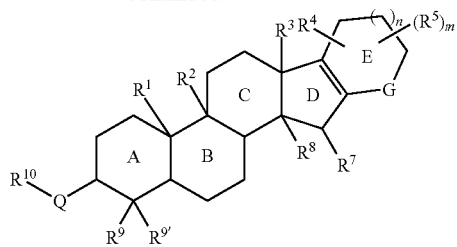

wherein each variable is as defined below and described in various embodiments below and herein.

According to one embodiment, the present invention provides a method for preparing a compound of formula I:

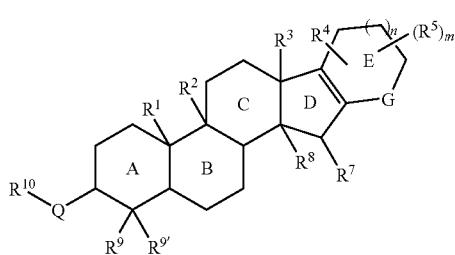

or a pharmaceutically acceptable salt thereof, wherein:
each of Ring A, Ring B, Ring C, Ring D, and Ring E is independently saturated, partially unsaturated or aromatic;
G is S, $CH_2$, NR, or O;
$R^1$ and $R^2$ are each independently halogen, R, OR, a suitably protected hydroxyl group, SR, a suitably protected thiol group, $N(R)_2$, or a suitably protected amino group, or $R^1$ and $R^2$ are taken together to form a 3-7 membered saturated, partially unsaturated, or aryl ring having 0-2 heteroatoms independently selected from nitrogen, oxygen, or sulfur;
each R is independently hydrogen, an optionally substituted $C_{1-6}$ aliphatic group, or an optionally substituted 3-8 membered saturated, partially unsaturated, or aryl ring having 0-4 heteroatoms independently selected from nitrogen, oxygen, or sulfur, wherein:
  two R on the same nitrogen atom are optionally taken together with said nitrogen atom to form a 3-8 membered saturated, partially unsaturated, or aryl ring having 1-4 heteroatoms independently selected from nitrogen, oxygen, or sulfur;
n is 0-2;
$R^3$, $R^4$, $R^7$, and $R^8$ are each independently selected from halogen, R, OR, a suitably protected hydroxyl group, SR, a suitably protected thiol group, $SO_2R$, $OSO_2R$, $N(R)_2$, a suitably protected amino group, NR(CO)R, NR(CO)(CO)R, $NR(CO)N(R)_2$, NR(CO)OR, (CO)OR, O(CO)R, $(CO)N(R)_2$, or $O(CO)N(R)_2$;
m is 0-2;
$R^5$ is $T-C(R')_3$, $T-C(R')_2C(R'')_3$, R, OR, a suitably protected hydroxyl group, SR, a suitably protected thiol group, $SO_2R$, $OSO_2R$, $N(R)_2$, a suitably protected amino group, NR(CO)R, NR(CO)(CO)R, $NR(CO)N(R)_2$, NR(CO)OR, (CO)OR, O(CO)R, $(CO)N(R)_2$, or $O(CO)N(R)_2$, or:
each T is independently a valence bond or an optionally substituted straight or branched, saturated or unsaturated, $C_{1-6}$ alkylidene chain wherein up to two methylene units of T are optionally and independently replaced by —O—, —N(R)—, —S—, —C(O)—, —S(O)—, or —S(O)$_2$—;
each R' and R" is independently selected from R, OR, SR, $SO_2R$, $OSO_2R$, $N(R)_2$, NR(CO)R, NR(CO)(CO)R, $NR(CO)N(R)_2$, NR(CO)OR, (CO)OR, O(CO)R, $(CO)N(R)_2$, or $O(CO)N(R)_2$;
$R^9$ and $R^{9'}$ are each independently selected from halogen, R, OR, SR, or $N(R)_2$, or $R^1$ and $R^2$ are taken together to form a 3-7 membered saturated, partially unsaturated, or aryl ring having 0-2 heteroatoms independently selected from nitrogen, oxygen, or sulfur;
Q is a valence bond or an optionally substituted straight or branched, saturated or unsaturated, $C_{1-6}$ alkylidene chain wherein up to two methylene units of Q are optionally and independently replaced by —O—, —N(R)—, —S—, —C(O)—, —S(O)—, or —S(O)$_2$—; and
$R^{10}$ is R, a suitably protected hydroxyl group, a suitably protected thiol group, a suitably protected amino group, an optionally substituted 3-8 membered saturated, partially unsaturated, or aryl monocyclic ring having 0-4 heteroatoms independently selected from nitrogen, oxygen, or sulfur, an optionally substituted 8-10 membered saturated, partially unsaturated, or aryl bicyclic ring having 0-4 heteroatoms independently selected from nitrogen, oxygen, or sulfur, a detectable moiety, a polymer residue, a peptide, or a sugar-containing or sugar-like moiety,
comprising the steps of:
(a) providing a compound of formula II:

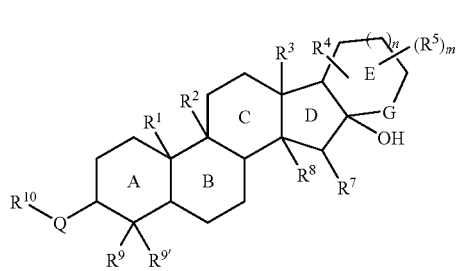

and
(b) converting the compound of formula II to the compound of formula I.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th Ed., Ed.: Smith, M. B. and March, J., John Wiley & Sons, New York: 2001, the entire contents of which are hereby incorporated by reference.

As defined generally above, each of Ring A, Ring B, Ring C, Ring D, and Ring E is independently saturated, partially unsaturated or aromatic. It will be appreciated that compounds of the present invention are contemplated as chemically feasible compounds. Accordingly, it will be understood by one of ordinary skill in the art that when any of Ring A, Ring B, Ring C, Ring D, and Ring E is unsaturated, then certain substituents on that ring will be absent in order to satisfy general rules of valency. For example, if Ring D is unsaturated at the bond between Ring D and Ring C, then $R^8$ and $R^3$ will be absent. All combinations of saturation and unsaturation of any of Ring A, Ring B, Ring C, Ring D, and Ring E are contemplated by the present invention. Thus, in order to satisfy general rules of valency, and depending on the degree of saturation or unsaturation of any of Ring A, Ring B, Ring C, Ring D, and Ring E, the requisite presence or absence of each of $R^1$, $R^2$, $R^3$, $R^4$, $R^5$, $R^7$, $R^8$, $R^9$, $R^{9'}$, and $QR^{10}$ is contemplated accordingly.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-6 aliphatic carbon atoms. In yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl. In other embodiments, an aliphatic group may have two geminal hydrogen atoms replaced with oxo (a bivalent carbonyl oxygen atom =O), or a ring-forming substituent, such as —O-(straight or branched alkylene or alkylidene)-O— to form an acetal or ketal.

In certain embodiments, exemplary aliphatic groups include, but are not limited to, ethynyl, 2-propynyl, 1-propenyl, 2-butenyl, 1,3-butadienyl, 2-pentenyl, vinyl (ethenyl), allyl, isopropenyl, methyl, ethyl, propyl, isopropyl, cyclopropyl, butyl, isobutyl, sec-butyl, tert-butyl, pentyl, isopentyl, sec-pentyl, neo-pentyl, tert-pentyl, cyclopentyl, hexyl, isohexyl, sec-hexyl, cyclohexyl, 2-methylpentyl, tert-hexyl, 2,3-dimethylbutyl, 3,3-dimethylbutyl, 1,3-dimethylbutyl, and 2,3-dimethylbut-2-yl.

The term "heterocycle," "heterocyclyl," "heterocycloaliphatic," or "heterocyclic" as used herein means non-aromatic, monocyclic, bicyclic, or tricyclic ring systems in which one or more ring members is an independently selected heteroatom. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl," "aralkoxy," or "aryloxyalkyl," refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring." The term "aryl" also refers to heteroaryl ring systems as defined hereinbelow.

The term "heteroaryl," used alone or as part of a larger moiety as in "heteroaralkyl" or "heteroarylalkoxy," refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic."

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; $N_3$, CN, $R^o$; $OR^o$; $SR^o$; 1,2-methylene-dioxy; 1,2-ethylenedioxy; phenyl (Ph) optionally substituted with $R^o$; —O(Ph) optionally substituted with $R^o$; $(CH_2)_{1-2}$(Ph), optionally substituted with $R^o$; CH=CH(Ph), optionally substituted with $R^o$; $NO_2$; CN; $N(R^o)_2$; $NR^oC(O)R^o$; $NR^oC(O)N(R^o)_2$; $NR^oCO_2R^o$; —$NR^oNR^oC(O)R^o$; $NR^oNR^oC(O)N(R^o)_2$; $NR^oNR^oCO_2R^o$; $C(O)C(O)R^o$; $C(O)CH_2C(O)R^o$; $CO_2R^o$; $C(O)R^o$; $C(O)N(R^o)_2$; $OC(O)N(R^o)_2$; $S(O)_2R^o$; $SO_2N(R^o)_2$; $S(O)R^o$; $NR^oSO_2N(R^o)_2$; $NR^oSO_2R^o$; $C(=S)N(R^o)_2$; $C(=NH)$—$N(R^o)_2$; or $(CH_2)_{0-2}NHC(O)R^o$ wherein each independent occurrence of $R^o$ is selected from hydrogen, optionally substituted $C_{1-6}$ aliphatic, an unsubstituted 5-6 membered heteroaryl or heterocyclic ring, phenyl, O(Ph), or $CH_2$(Ph), or, notwithstanding the definition above, two independent occurrences of R°, on the same substituent or different substituents, taken together with the atom(s) to which each R° group is bound, form a 3-8 membered cycloalkyl, heterocyclyl, aryl, or heteroaryl ring having 0-4 heteroatoms independently selected from nitrogen, oxygen, or sulfur. Optional substituents on the aliphatic group of R° are selected from $N_3$, CN, $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), $O(haloC_{1-4}$ aliphatic), or $haloC_{1-4}$ aliphatic, wherein each of the foregoing $C_{1-4}$ aliphatic groups of R° is unsubstituted.

An aliphatic or heteroaliphatic group or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$ aliphatic groups of R* is unsubstituted.

Optional substituents on the nitrogen of a non-aromatic heterocyclic ring are selected from $R^+$, $N(R^+)_2$, $C(O)R^+$, $CO_2R^+$, $C(O)C(O)R^+$, $C(O)CH_2C(O)R^+$, $SO_2R^+$, $SO_2N(R^+)_2$, $C(=S)N(R^+)_2$, $C(=NH)—N(R^+)_2$, or $NR^+SO_2R^+$; wherein $R^+$ is hydrogen, an optionally substituted $C_{1-6}$ aliphatic, optionally substituted phenyl, optionally substituted O(Ph), optionally substituted $CH_2$(Ph), optionally substituted $(CH_2)_{1-2}$(Ph); optionally substituted CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-4 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$ aliphatic groups of $R^+$ is unsubstituted.

As detailed above, in some embodiments, two independent occurrences of R° (or $R^+$, or any other variable similarly defined herein), are taken together with the atom(s) to which each variable is bound to form a 3-8-membered cycloalkyl, heterocyclyl, aryl, or heteroaryl ring having 0-4 heteroatoms independently selected from nitrogen, oxygen, or sulfur. Exemplary rings that are formed when two independent occurrences of R° (or $R^+$, or any other variable similarly defined herein) are taken together with the atom(s) to which each variable is bound include, but are not limited to the following: a) two independent occurrences of R° (or $R^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or $R^+$, or any other variable similarly defined herein) that are bound to different atoms and are taken together with both of those atoms to form a ring, for example where a phenyl group is substituted with two occurrences of OR°

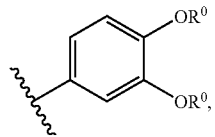

these two occurrences of R° are taken together with the oxygen atoms to which they are bound to form a fused 6-membered oxygen containing ring:

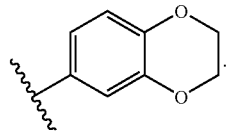

It will be appreciated that a variety of other rings can be formed when two independent occurrences of R° (or $R^+$, or any other variable similarly defined herein) are taken together with the atom(s) to which each variable is bound and that the examples detailed above are not intended to be limiting.

As used herein, the term "detectable moiety" is used interchangeably with the term "label" and relates to any moiety capable of being detected, e.g., primary labels and secondary labels. Primary labels, such as radioisotopes (e.g., $^{32}P$, $^{33}P$, $^{35}S$, or $^{14}C$), mass-tags, and fluorescent labels are signal generating reporter groups which can be detected without further modifications.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label," "fluorescent dye," and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethylrhodamine (TMR), Carboxytetramethylrhodamine (TAMRA), Texas Red, and Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The term "substrate," as used herein refers to any material or macromolecular complex to which a functionalized end-group of a compound of the present invention can be attached. Examples of commonly used substrates include, but are not limited to, glass surfaces, silica surfaces, plastic surfaces, metal surfaces, surfaces containing a metallic or chemical coating, membranes (eg., nylon, polysulfone, silica), microbeads (e.g., latex, polystyrene, or other polymer), porous polymer matrices (e.g., polyacrylamide gel, polysaccharide, polymethacrylate), and macromolecular complexes (e.g., protein, polysaccharide).

Unless otherwise stated, structures depicted herein are also meant to include all isomeric (e.g., enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

3. Description of Exemplary Embodiments

As described generally above, the present invention provides a method for preparing a compound of formula I:

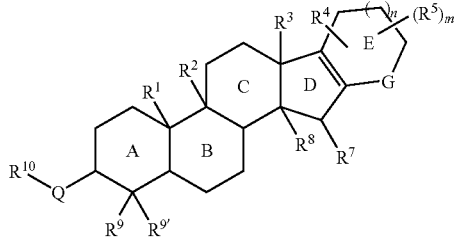

comprising the steps of:
(a) providing a compound of formula II:

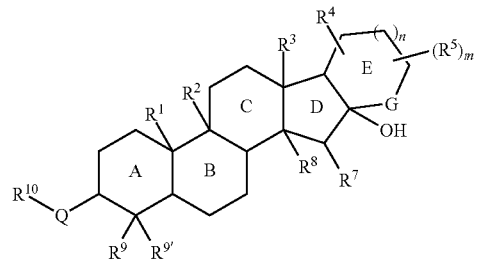

and
(b) converting the compound of formula II to the compound of formula I.

One of ordinary skill in the art will recognize that the conversion of a compound of formula II to a compound of formula I is readily accomplished by an intramolecular dehydration reaction. Such dehydration reactions are known to one of ordinary skill in the art and involve the loss of a water molecule to form a double bond.

In certain embodiments, the conversion of a compound of formula II to a compound of formula I is achieved by treatment of the compound of formula II with a suitable acid. As used herein, the phrase "suitable acid" refers to an organic or inorganic acid in an amount sufficient to accomplish the dehydration of a compound of formula II to form a compound of formula I. Such suitable acids are well known in the art and include inorganic acids, e.g. hydrochloric acid, hydrobromic acid, phosphoric acid, nitric acid, sulfuric acid or perchloric acid, or organic acids, e.g. acetic acid, oxalic acid, maleic acid, tartaric acid, citric acid, succinic acid, malonic acid, lower alkyl sulfonic acids or aryl sulfonic acids. In certain embodiments, the suitable acid is a Brønsted acid, such as hydrogen halides, carboxylic acids, sulfonic acids, sulfuric acid, and phosphoric acid. In certain embodiments, the suitable acid is TFA.

The conversion of a compound of formula II to a compound of formula I is optionally performed in the presence of a suitable solvent. A suitable solvent is a single solvent or a solvent mixture that, in combination with the reagents, may facilitate the progress of the reaction therebetween. The suitable solvent may solubilize one or more of the reaction components, or, alternatively, the suitable solvent may facilitate the agitation of a suspension of one or more of the reaction components. Examples of suitable solvents useful in the present invention are a protic solvent, a halogenated hydrocarbon, an ether, an ester, an aromatic hydrocarbon, a polar or a non-polar aprotic solvent, or any mixtures thereof. Such mixtures include, for example, mixtures of protic and non-protic solvents such as benzene/methanol/water; benzene/water; DME/water, and the like. In certain embodiments, the suitable solvent is a polar aprotic solvent, such as an alcohol.

In certain embodiments, the suitable acid may also serve as the suitable solvent.

In certain embodiments, the conversion of a compound of formula II to a compound of formula I is performed with optional heating.

As defined generally above, the G moiety of formulae I and II is S, $CH_2$, NR, or O. In certain embodiments, the G moiety of formulae I and II is O.

As defined generally above, $R^1$ and $R^2$ of formulae I and II are each independently halogen, R, OR, a suitably protected hydroxyl group, SR, a suitably protected thiol group, N(R)$_2$, or a suitably protected amino group, or R$^1$ and R$^2$ are taken together to form a 3-7 membered saturated, partially unsaturated, or aryl ring having 0-2 heteroatoms independently selected from nitrogen, oxygen, or sulfur. In certain embodiments, R$^1$ and R$^2$ of formulae I and II are each independently R or OR. In other embodiments, R$^1$ and R$^2$ of formulae I and II are each independently R, wherein R is hydrogen or an optionally substituted C$_{1-6}$ aliphatic group. According to another aspect of the present invention, R$^1$ and R$^2$ of formulae I and II are taken together to form a 3-6 membered saturated, partially unsaturated, or aryl ring having 0-2 heteroatoms independently selected from nitrogen, oxygen, or sulfur. Yet another aspect of the present invention provides a compound of formulae I and II wherein R$^1$ and R$^2$ are taken together to form a 3-6 membered saturated carbocyclic ring. In other embodiments, R$^1$ and R$^2$ of formula I are taken together to form a cyclopropyl ring.

In certain embodiments, the n moiety of formulae I and II is 0-1. In other embodiments, the n moiety of formula I and II is 1.

As defined generally above, the R$^5$ group of formulae I and II is R$^5$ is T-C(R')$_3$, T-C(R')$_2$C(R'')$_3$, R, OR, a suitably protected hydroxyl group, SR, a suitably protected thiol group, SO$_2$R, OSO$_2$R, N(R)$_2$, a suitably protected amino group, NR(CO)R, NR(CO)(CO)R, NR(CO)N(R)$_2$, NR(CO)OR, (CO)OR, O(CO)R, (CO)N(R)$_2$, or O(CO)N(R)$_2$, wherein each T is independently a valence bond or an optionally substituted straight or branched, saturated or unsaturated, C$_{1-6}$ alkylidene chain wherein up to two methylene units of T are optionally and independently replaced by —O—, —N(R)—, —S—, —C(O)—, —S(O)—, or —S(O)$_2$—. In certain embodiments, each T is independently a valence bond or a straight or branched C$_{1-4}$ alkylidene chain wherein one methylene unit of T is optionally replaced by —O—, —N(R)—, or —S—. In other embodiments, each T is independently a valence bond or a straight or branched C$_{1-4}$ alkylidene chain. In still other embodiments, each T is a valence bond.

When the R$^5$ group of formulae I and II is T-C(R')$_3$ or T-C(R')$_2$C(R'')$_3$, each R' and R'' is independently selected from R, OR, SR, SO$_2$R, OSO$_2$R, N(R)$_2$, NR(CO)R, NR(CO)(CO)R, NR(CO)N(R)$_2$, NR(CO)OR, (CO)OR, O(CO)R, (CO)N(R)$_2$, or O(CO)N(R)$_2$. In certain embodiments, each R' and R'' is independently R, OR, OC(O)R, SR, or N(R)$_2$. In other embodiments, each R' and R'' is independently R, OR, or OC(O)R. Exemplary R' and R'' groups include hydrogen, CH$_3$, OH, and OC(O)CH$_3$.

As defined generally above, the R$^5$ group of formulae I and II is, inter alia, a suitably protected hydroxyl group, a suitably protected thiol group, or a suitably protected amino group. Hydroxylprotecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups of the R$^5$ group of formulae I and II further include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl.

Thiol protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitably protected thiol groups of the R$^5$ moiety of formulae I and II include, but are not limited to, disulfides, thioethers, silyl thioethers, thioesters, thiocarbonates, thiocarbamates, and the like. Examples of such groups include, but are not limited to, alkyl thioethers, benzyl and substituted benzyl thioethers, triphenylmethyl thioethers, and trichloroethoxycarbonyl, to name but a few.

According to another aspect of the present invention, the R$^5$ moiety of formulae I and II is a thiol protecting group that is removable under neutral conditions e.g. with AgNO$_3$, HgCl$_2$, and the like. Other neutral conditions include reduction using a suitable reducing agent. Suitable reducing agents include dithiothreitol (DTT), mercaptoethanol, dithionite, reduced glutathione, reduced glutaredoxin, reduced thioredoxin, substituted phosphines such as tris carboxyethyl phosphine (TCEP), and any other peptide or organic based reducing agent, or other reagents known to those of ordinary skill in the art. According to yet another aspect of the present invention, the R$^5$ moiety of formulae I and II is a thiol protecting group that is "photocleavable". Such suitable thiol protecting groups are known in the art and include, but are not limited to, a nitrobenzyl group, a tetrahydropyranyl (THP) group, a trityl group, —CH$_2$SCH$_3$ (MTM), dimethylmethoxymethyl, or —CH$_2$—S—S-pyridin-2-yl. One of ordinary skill in the art would recognize that many of the suitable hydroxyl protecting groups, as described herein, are also suitable as thiol protecting groups.

In certain embodiments, the R$^5$ group of formulae I and II is a suitably protected amino group. Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitably protected amino groups of said R$^5$ moiety further include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like. In certain embodiments, the amino protecting group of the R$^5$ moiety is phthalimido. In still other embodiments, the amino protecting group of the R$^5$ moiety is a tert-butyloxycarbonyl (BOC) group.

As defined generally above, the Q group of formulae I and II is a valence bond or an optionally substituted straight or branched, saturated or unsaturated, $C_{1-4}$ alkylidene chain wherein up to two methylene units of Q are optionally and independently replaced by —O—, —N(R)—, —S—, —C(O)—, —S(O)—, or —S(O)$_2$—. In certain embodiments, Q is a an optionally substituted straight or branched, saturated or unsaturated, $C_{1-2}$ alkylidene chain wherein up to one methylene unit of Q is optionally replaced by —O—, —N(R)—, or —S—. In other embodiments, Q is —O—.

As defined generally above, the $R^{10}$ group of formulae I and II is R, a suitably protected hydroxyl group, a suitably protected thiol group, a suitably protected amino group, an optionally substituted 3-8 membered saturated, partially unsaturated, or aryl monocyclic ring having 0-4 heteroatoms independently selected from nitrogen, oxygen, or sulfur, an optionally substituted 8-10 membered saturated, partially unsaturated, or aryl bicyclic ring having 0-4 heteroatoms independently selected from nitrogen, oxygen, or sulfur, a detectable moiety, a polymer residue, a peptide, or a sugar-containing group, or a sugar-like group.

In certain embodiments, the $R^{10}$ group of formulae I and II is a sugar-containing group. Such sugar-containing groups are well known to one of ordinary skill in the art and include those described in detail in "Essentials of Glycobiology" Edited by Varki, A., et al., Cold Spring Harbor Laboratory Press. Cold Spring Harbor, N.Y. 2002. In certain embodiments, the $R^{10}$ group of formulae I and II is a glycoside. Exemplary $R^{10}$ groups include arabinopyranosides and xylopyranosides. In certain embodiments, the $R^{10}$ group of formulae I and II is a xylopyranoside. In certain embodiments, the $R^{10}$ group of formulae I and II is an arabinopyranoside. In still other embodiments, the $R^{10}$ group of formulae I and II is

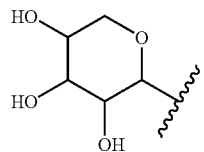

According to another embodiment, the $R^{10}$ group of formulae I and II is

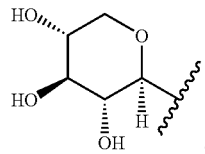

Yet another embodiment provides a compound of formulae I and II wherein $R^{10}$ is

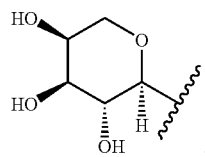

According to another aspect of the present invention, the $R^{10}$ group of formulae I and II is a sugar-mimetic. Such sugar-mimetics are well known to one of ordinary skill in the art and include those described in detail in "Essentials of Glycobiology." For example, sugar-mimetic groups contemplated by the present invention include cyclitols and the like. In certain embodiments, $R^{10}$ is a cyclitol moiety, wherein said cyclitol is a cycloalkane containing one hydroxyl group on each of three or more ring atoms, as defined by IUPAC convention. In other embodiments, such cyclitol moieties include inositols such as scyllo-inositol.

In addition, suitable sugar-like moieties of the $R^{10}$ group of formulae I and II include acyclic sugar groups. Such groups include linear alkylols and erythritols, to name but a few. It will be appreciated that sugar groups can exist in either cyclic or acyclic form. Accordingly, acyclic forms of a sugar group are contemplated by the present invention as a suitable sugar-like moiety of the $R^{10}$ group of formulae I and II.

In certain embodiments, the $R^{10}$ group of formulae I and II is a detectable moiety. In other embodiments, the $R^{10}$ group of formulae I and II is a fluorescent label, fluorescent dye, or fluorophore as defined herein, supra.

According to another aspect of the present invention, the $R^{10}$ group of formulae I and II is a polymer residue. Polymer residues are well known in the art and include those described in detail in "Chemistry of Protein Conjugation and Cross-Linking" Shan S. Wong, CRC Press. Boca Raton, Fla. 1991. Suitable polymer residues of the $R^{10}$ group of formulae I and II include poly(alkylene oxides), such as PEG, poly(amino acids), and other polymer residues capable of conjugation to a compound of the present invention.

As defined generally above, the $R^{10}$ group of formulae I and II is, inter alia, a suitably protected hydroxyl group, a suitably protected thiol group, or a suitably protected amino group. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitable hydroxyl protecting groups of the $R^{10}$ group of formulae I and II further include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl.

Thiol protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable thiol protecting groups of the $R^{10}$ moiety of formulae I and II include, but are not limited to, disulfides, thioethers, silyl thioethers, thioesters, thiocarbonates, thiocarbamates, and the like. Examples of such groups include, but are not limited to, alkyl thioethers, benzyl and substituted benzyl thioethers, triphenylmethyl thioethers, trichloroethoxycarbonyl, to name but a few.

According to another aspect of the present invention, the $R^{10}$ moiety of formulae I and II is a thiol protecting group that is removable under neutral conditions e.g. with $AgNO_3$, $HgCl_2$, and the like. Other neutral conditions include reduction using a suitable reducing agent. Suitable reducing agents include dithiothreitol (DTT), mercaptoethanol, dithionite, reduced glutathione, reduced glutaredoxin, reduced thioredoxin, substituted phosphines such as tris carboxyethyl phosphine (TCEP), and any other peptide or organic based reducing agent, or other reagents known to those of ordinary skill in the art. According to yet another aspect of the present invention, the $R^{10}$ moiety of formulae I and II is a thiol protecting group that is "photocleavable." Such suitable thiol protecting groups are known in the art and include, but are not limited to, a nitrobenzyl group, a tetrahydropyranyl (THP) group, a trityl group, —$CH_2SCH_3$ (MTM), dimethylmethoxymethyl, or —$CH_2$—S—S-pyridin-2-yl. One of ordinary skill in the art would recognize that many of the suitable hydroxyl protecting groups, as described herein, are also suitable as thiol protecting groups.

In certain embodiments, the $R^{10}$ group of formulae I and II is a suitably protected amino group. Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups of said $R^{10}$ moiety further include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like. In certain embodiments, the amino protecting group of the $R^{10}$ moiety is phthalimido. In still other embodiments, the amino protecting group of the $R^{10}$ moiety is a tert-butyloxycarbonyl (BOC) group.

As described generally above, the present invention provides a method for preparing a compound of formula I:

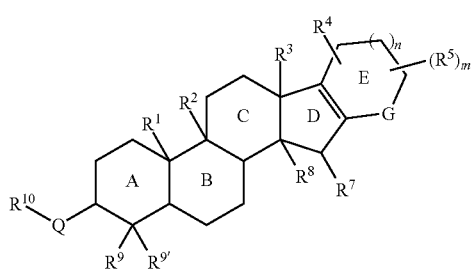

or a pharmaceutically acceptable salt thereof, wherein each variable is defined above and in classes and subclasses described above and herein. In certain embodiments, the present invention provides a method for preparing a compound of formula I having the stereochemistry as depicted in formula I-a:

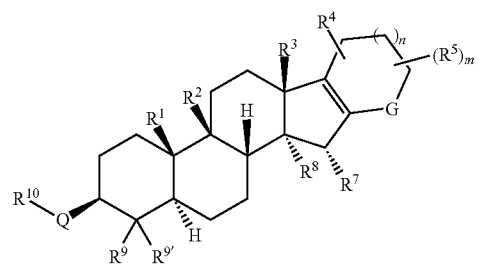

or a pharmaceutically acceptable salt thereof, wherein each variable is defined above and in classes and subclasses described above and herein for compounds of formula I.

In certain embodiments, the present invention provides a method for preparing a compound of formula I, as described herein, wherein said compound is of formula I-b:

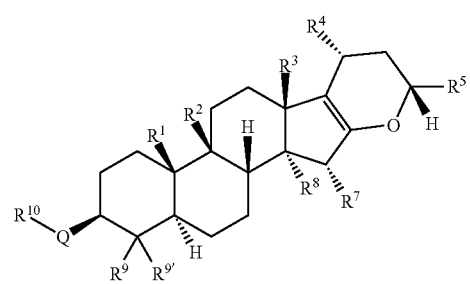

or a pharmaceutically acceptable salt thereof, wherein each variable is defined above and in classes and subclasses described above and herein for compounds of formula I.

In other embodiments, the present invention provides a method for preparing a compound of formula I, as described herein, wherein said compound is of formula I-c:

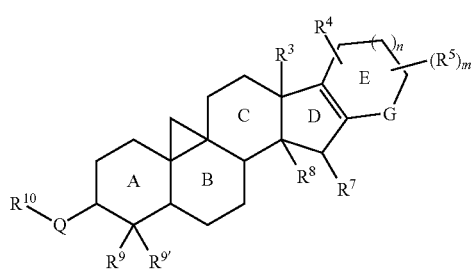

or a pharmaceutically acceptable salt thereof, wherein each variable is defined above and in classes and subclasses described above and herein for compounds of formula I.

As defined generally above, each of Ring A, Ring B, Ring C, Ring D, and Ring E is independently saturated, partially unsaturated or aromatic. In certain embodiments, the present invention provides a method of preparing a compound of formula I wherein Ring B is unsaturated and $R^1$ and $R^2$ are absent, thus forming a compound of formula I-d:

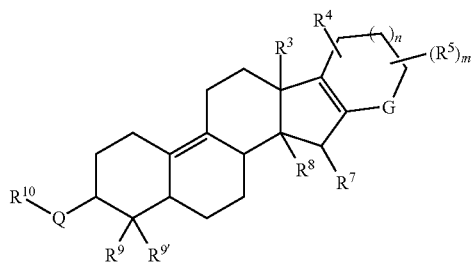

I-d or a pharmaceutically acceptable salt thereof, wherein each variable is defined above and in classes and subclasses described above and herein for compounds of formula I.

In certain embodiments, the n group of formula I-d is 0-1 and the G group of formula I-d is oxygen.

In other embodiments, the present invention provides a method for preparing compound of formula I-i:

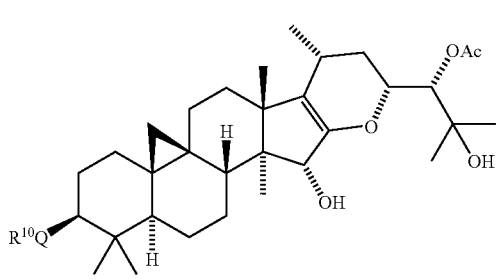

I-i or a pharmaceutically acceptable salt thereof, wherein:

Q is a valence bond or an optionally substituted straight or branched, saturated or unsaturated, $C_{1-6}$ alkylidene chain wherein up to two methylene units of Q are optionally and independently replaced by —O—, —N(R)—, —S—, —C(O)—, —S(O)—, or —S(O)$_2$—;

$R^{10}$ is R, a suitably protected hydroxyl group, a suitably protected thiol group, a suitably protected amino group, an optionally substituted 3-8 membered saturated, partially unsaturated, or aryl monocyclic ring having 0-4 heteroatoms independently selected from nitrogen, oxygen, or sulfur, an optionally substituted 8-10 membered saturated, partially unsaturated, or aryl bicyclic ring having 0-4 heteroatoms independently selected from nitrogen, oxygen, or sulfur, a detectable moiety, a polymer residue, a peptide, or a sugar-containing or sugar-like moiety; and R is hydrogen, an optionally substituted $C_{1-6}$ aliphatic group, or an optionally substituted 3-8 membered saturated, partially unsaturated, or aryl ring having 0-4 heteroatoms independently selected from nitrogen, oxygen, or sulfur, wherein:

two R on the same nitrogen atom are optionally taken together with said nitrogen atom to form a 3-8 membered saturated, partially unsaturated, or aryl ring having 1-4 heteroatoms independently selected from nitrogen, oxygen, or sulfur, comprising the steps of:

(a) providing a compound of formula I-ii:

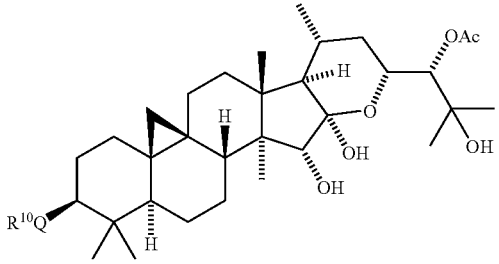

I-ii and (b) converting compound I-ii to compound I-i.

In other embodiments, the present invention provides a method for preparing compound of formula I-iii:

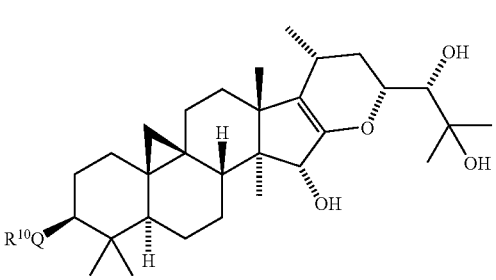

I-iii or a pharmaceutically acceptable salt thereof, wherein:

Q is a valence bond or an optionally substituted straight or branched, saturated or unsaturated, $C_{1-6}$ alkylidene chain wherein up to two methylene units of Q are optionally and independently replaced by —O—, —N(R)—, —S—, —C(O)—, —S(O)—, or —S(O)$_2$—;

$R^{10}$ is R, a suitably protected hydroxyl group, a suitably protected thiol group, a suitably protected amino group, an optionally substituted 3-8 membered saturated, partially unsaturated, or aryl monocyclic ring having 0-4 heteroatoms independently selected from nitrogen, oxygen, or sulfur, an optionally substituted 8-10 membered saturated, partially unsaturated, or aryl bicyclic ring having 0-4 heteroatoms independently selected from nitrogen, oxygen, or sulfur, a detectable moiety, a polymer residue, a peptide, or a sugar-containing or sugar-like moiety; and R is hydrogen, an optionally substituted $C_{1-6}$ aliphatic group, or an optionally substituted 3-8 membered saturated, partially unsaturated, or aryl ring having 0-4 heteroatoms independently selected from nitrogen, oxygen, or sulfur, wherein:

two R on the same nitrogen atom are optionally taken together with said nitrogen atom to form a 3-8 membered saturated, partially unsaturated, or aryl ring having 1-4 heteroatoms independently selected from nitrogen, oxygen, or sulfur, comprising the steps of:
(a) providing a compound of formula I-iv:

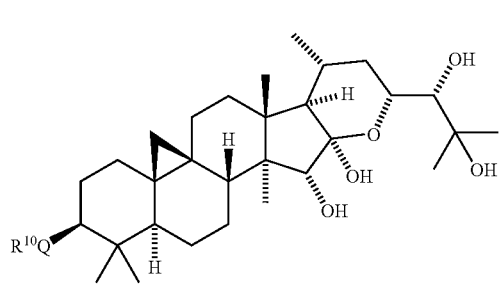

and
(b) converting compound I-iv to compound I-iii.

4. General Methods of Providing the Present Compounds

The compounds of formula II of this invention may be prepared or isolated in general by synthetic and/or semi-synthetic methods known to those skilled in the art for analogous compounds and by methods described in detail in the Examples, below.

In certain embodiments, methods of the present invention for converting a compound of formula II to a compound of formula I are performed using an isolated compound of formula II. Isolated compounds of formula II may be provided by purification/separation from an extract of black cohosh root. Alternatively, isolated compounds of formula II may be provided by total synthesis or semi-synthesis. In other embodiments, the conversion of a compound of formula II to a compound of formula I is performed using an extract of black cohosh root that is enriched in a compound of formula II. Such isolation methods and enriched extracts are described in more detail below.

Isolation of Components

Certain compounds of the present invention were isolated from black cohosh root, also known as *cimicifuga racemosa* or *actaea racemosa*, and the structure of these compounds elucidated. Commercial extracts, powders, and capsules of black cohosh root are available for treating a variety of menopausal and gynecological disorders. However, it has been surprisingly found that certain compounds present in black cohosh root are useful for modulating and/or inhibiting amyloid-beta peptide production. In particular, certain compounds have been isolated from black cohosh root and identified, wherein these compounds are useful for modulating and/or inhibiting amyloid-beta peptide production especially amyloid-beta peptide (1-42). Such compounds are encompassed by formulae I and II. These compounds may be isolated and utilized in a form substantially free of other compounds normally found in the root. Alternatively, an extract may be prepared from the root wherein said extract is enriched in a compound of the present invention.

As described above and herein, certain compounds useful in methods of the present invention are isolated from standard extracts of cultivated or wild-grown black cohosh roots and rhizomes. It is also contemplated that the present compounds may also be isolated from plant root tissue grown in culture or from the culture medium of the culture plant tissue. Such methods of growing plant root tissue in culture are well known to one of ordinary skill in the art and include those described in Hairy Roots, Culture and Applications, edited by Pauline M. Doran, published by Harwood Academic Publishers, Amsterdam, The Netherlands. Copyright 1997 OPA (Overseas Publishers Association) Amsterdam B. V. ISBN 90-5702-117-X, the entirety of which is hereby incorporated herein by reference.

Alternatively, compounds of the present invention may be prepared by semi-synthetic processes starting from other compounds found in extracts of black cohosh and related *cimicifuga* species, whether from roots and rhizome or aerial parts of these plants. One of ordinary skill in the art will recognize that synthetic precursors may be obtained from one or more *cimicifuga* species including, but not limited to, *Cimicifuga racemosa*, *Cimicifuga dahurica*, *Cimicifuga foetida*, *Cimicifuga heracleifolia*, *Cimicifuga japonica*, *Cimicifuga acerina*, *Cimicifuga acerima*, *Cimicifuga simplex*, and *Cimicifuga elata*, *Cimicifuga calthaefolia*, *Cimicifuga frigida*, *Cimicifuga laciniata*, *Cimicifuga mairei*, *Cimicifuga rubifolia*, *Cimicifuga americana*, *Cimicifuga biternata*, and *Cimicifuga bifida* or a variety thereof. This may be accomplished either by chemical or biological transformation of an isolated compound or an extract fraction or mixture of compounds. Chemical transformation may be accomplished by, but not limited to, manipulation of temperature, pH, and/or treatment with various solvents. Biological transformation may be accomplished by, but not limited to, treatment of an isolated compound or an extract fraction or mixture of compounds with plant tissue, plant tissue extracts, other microbiological organisms or an isolated enzyme from any organism.

In certain embodiments, the present invention provides an extract of black cohosh root wherein said extract comprises at least 10% by weight of a compound of the present invention. In other embodiments, the present invention provides an extract of black cohosh root wherein said extract comprises from about 10% by weight to about 50% by weight of a compound of the present invention. In still other embodiments, the present invention provides an extract of black cohosh root wherein said extract comprises from about 10% by weight to about 50% by weight of a compound of the present invention, wherein said extract is substantially free of actein.

According to another embodiment, the present invention provides a compound of formula II, for use in methods of the present invention, substantially free of other compounds found in black cohosh root. As used herein, the term "substantially free" means that the compound is made up of a significantly greater proportion of a compound of formula II as compared with the compound as found in black cohosh root or extracts thereof. In some embodiments, the present invention provides a compound of formula II in an amount of about 1 weight percent to about 99 weight percent. In certain embodiments, the compound of formula II is provided in greater than about 80% chemical purity. In other embodiments, the compound of formula II is provided in greater than about 90% chemical purity. In other embodiments, the compound of formula II contains no more than about 10.0 area percent HPLC of other components of black cohosh root relative to the total area of the HPLC chromatogram. In other embodiments, the compound of formula II contains no more than about 8.0 area percent HPLC of other components of black cohosh root relative to the total area of the HPLC chromatogram, and in still other embodiments, no more than about 3 area percent.

Methods to determine whether the compounds of the present invention are in a form substantially free of other compounds normally found in black cohosh root are known to one of ordinary skill in the art as described below. Compounds that were previously isolated, and identified, from black cohosh root include certain cycloartanol-based triterpenes including acteol, acetylacteol, 26-deoxyacteol, cimigenol, actein, 26-deoxyactein, and cimicifugoside. (E)-Isoferulic acid and the isoflavone formononetin have also been isolated and identified. Representatives of these compounds have the following structures:

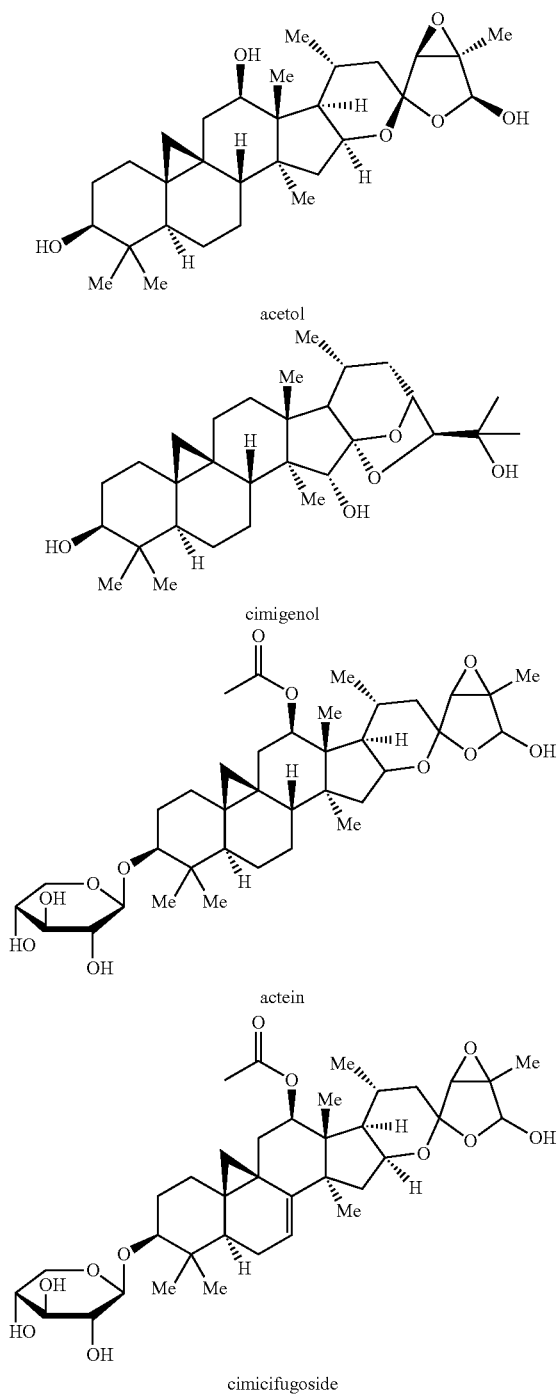

acetol cimigenol actein cimicifugoside

Accordingly, another embodiment of the present invention provides a compound of formula II, useful in methods of the present invention, substantially free of one or more of acteol, acetylacteol, 26-deoxyacteol, cimigenol, actein, 26-deoxyactein, and cimicifugoside. In certain embodiments, the present invention provides a compound of formula II, for use in methods of the present invention, substantially free of acteol, acetylacteol, 26-deoxyacteol, cimigenol, actein, 26-deoxyactein, and cimicifugoside.

According to another embodiment, the present invention provides an extract of black cohosh root enriched in a compound of formula II, useful in methods of the present invention, with a diminished amount of one or more of acteol, acetylacteol, 26-deoxyacteol, cimigenol, actein, 26-deoxyactein, and cimicifugoside. According to yet another embodiment, the present invention provides an extract of black cohosh root enriched in a compound of formula II, useful in methods of the present invention, with a diminished amount of each of acteol, acetylacteol, 26-deoxyacteol, cimigenol, actein, 26-deoxyactein, and cimicifugoside.

A variety of techniques are well known in the art for extracting, isolating, and/or purifying individual active components of black cohosh root. The present invention encompasses both the identification of such active components as described herein and the incorporation of such components into the compositions of the present invention as described herein.

Individual active components of black cohosh extracts may be identified as described herein and may be isolated and/or purified using any techniques known in the art. The active component may be purified from the root itself in any form or the decoction of a mixture of an extract of the present invention or a commercially available extract, among others. Various techniques that may be employed in the purification include filtration, selective precipitation, extraction with organic solvents, extraction with aqueous solvents, column chromatography (silica gel), high performance liquid chromatography (HPLC) and other methods known to one of ordinary skill in the art.

According to certain embodiments, the present extracts useful in methods of the present invention are those using an isolated fraction from black cohosh root. An isolated fraction means a subsidiary amount of root substances which has been removed, for example, by chromatographic means, distillation, precipitation, extraction, filtration or in other ways from the root itself. In other embodiments, the root extracts and fractions are removed therefrom by chromatography, distillation, precipitation, or extraction. Such extraction and isolation techniques are well known to one of ordinary skill in the art. The details of some of these techniques are set forth in the Examples section below.

According to other embodiments of the present invention, the presence and purity of the active compound is assessed by chemical methods including nuclear magnetic resonance (NMR) spectroscopy, mass spectrometry, infrared spectroscopy (IR), ultra-violet visible spectroscopy, elemental analysis, and polarimetry, refractometry, to name but a few Such methods of analysis are known to one of ordinary skill in the art. In other embodiments, the chemical structure of active compounds isolated from black cohosh root is determined by methods known to one of ordinary skill in the art, including NMR, mass spectrometry, infrared spectroscopy (IR), ultra-violet visible spectroscopy, elemental analysis, polarimetry, refractometry, and X-ray crystallography, to name but a few.

Although certain exemplary embodiments are described above and herein, it will be appreciated that the root extracts of the present invention can be prepared according to the methods described generally above using appropriate starting materials by methods generally available to one of ordinary skill in the art.

5. Uses, Formulation and Administration

Pharmaceutically Acceptable Compositions

According to another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents. In certain embodiments, the present invention provides a composition comprising a compound of formula I, prepared by methods of the present invention, and a pharmaceutically acceptable carrier, adjuvant, or vehicle.

It will also be appreciated that certain compounds of the present invention can exist in free form for treatment, or where appropriate, as a pharmaceutically acceptable salt thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or a pharmaceutically active metabolite or residue thereof. As used herein, the term "pharmaceutically active metabolite or residue thereof" means that a metabolite or residue thereof is also a pharmaceutically active compound in accordance with the present invention.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl sulfonate and aryl sulfonate.

The compositions of the present invention may additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions provided by the present invention can be employed in combination therapies, that is the present compositions can be administered concurrently with, prior to, or subsequent to, one or more other desired therapeutic agents or medical procedures. The particular combination of therapies (therapeutic agents or procedures) to employ in a combination regimen will take into account compatibility of the desired therapeutic agents and/or procedures and the desired therapeutic effect to be achieved. It will also be appreciated that the therapies employed may achieve a desired effect for the same disorder (for example, a compound described herein may be administered concurrently with another therapeutic agent used to treat the same disorder), or they may achieve different effects (e.g., control of any adverse effects).

For example, known agents useful for treating neurodegenerative disorders may be combined with the compositions of this invention to treat neurodegenerative disorders, such as Alzheimer's disease. Examples of such known agents useful for treating neurodegenerative disorders include, but are not limited to, treatments for Alzheimer's disease such as acetylcholinesterase inhibitors, including donepezil, memantine (and related compounds as NMDA inhibitors), Exelon®; treatments for Parkinson's disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; riluzole, and anti-Parkinsonian agents. For a more comprehensive discussion of updated therapies useful for treating neurodegenerative disorders, see, a list of the FDA approved drugs at http://www.fda.gov, and The Merck Manual, Seventeenth Ed. 1999, the entire contents of which are hereby incorporated by reference.

In other embodiments, the compounds of the present invention are combined with other agents useful for treating neurodegenerative disorders, such as Alzheimer's disease, wherein such agents include beta-secretase inhibitors, gamma-secretase inhibitors, aggregation inhibitors, farnesyl transferase inhibitors, metal chelators, antioxidants, and neuroprotectants.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, prepared according to methods of the present invention, an additional therapeutic agent, and a pharmaceutically acceptable carrier, adjuvant, or vehicle.

Other examples of agents the inhibitors of this invention may also be combined with include, without limitation: treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. In certain embodiments, the amount of additional therapeutic agent in the present compositions will range from about 50% to 100% of the amount normally present in a composition comprising that agent as the only therapeutically active agent.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the present invention provides a composition containing a compound of formula I, prepared according to methods of the present invention, in an amount of about 1 weight percent to about 99 weight percent. In other embodiments, the composition containing a compound of formula I, prepared according to methods of the present invention, contains no more than about 10.0 area percent HPLC of other components of black cohosh root relative to the total area of the HPLC chromatogram. In other embodiments, the composition containing a compound of formula I, prepared according to methods of the present invention, contains no more than about 8.0 area percent HPLC of other components of black cohosh root relative to the total area of the HPLC chromatogram, and in still other embodiments, no more than about 3 area percent.

Uses of Compounds and Pharmaceutically Acceptable Compositions

The compounds prepared by methods of the present invention are useful for modulating and/or inhibiting amyloid-beta (1-42) peptide production in a patient. Accordingly, the compounds of the present invention are useful for treating, or lessening the severity of, disorders associated with amyloid-beta (1-42) peptide production in a patient.

The compounds, extracts, and compositions, according to the method of the present invention, may be administered using any amount and any route of administration effective for treating or lessening the severity of a neurodegenerative disorder. The exact amount required will vary from subject to subject, depending on the species, age, and general condition of the subject, the severity of the infection, the particular agent, its mode of administration, and the like.

In certain embodiments, the present invention provides a method for modulating and/or inhibiting amyloid-beta (1-42) peptide production in a patient, wherein said method comprises administering to said patient a compound of formula I, prepared according to methods of the present invention, or a pharmaceutically acceptable composition comprising said compound. In other embodiments, the present invention provides a method of selectively modulating and/or inhibiting amyloid-beta (1-42) peptide production in a patient, wherein said method comprises administering to said patient a compound of formula I, prepared according to methods of the present invention, or a pharmaceutically acceptable composition thereof. In still other embodiments, the present invention provides a method of reducing amyloid-beta (1-42) peptide levels in a patient, wherein said method comprises administering to said patient a compound of formula I, prepared according to methods of the present invention, or a pharmaceutically acceptable composition thereof. In other embodiments, the present invention provides a method for reducing amyloid-beta (1-42) peptide levels in a cell, comprising contacting said cell with a compound of formula I, prepared according to methods of the present invention. Another embodiment provides a method for reducing amyloid-beta (1-42) in a cell without substantially reducing amyloid-beta (1-40) peptide levels in the cell, comprising contacting said cell with a compound of formula I, prepared according to methods of the present invention. Yet another embodiment provides a method for reducing amyloid-beta (1-42) in a cell and increasing at least one of amyloid-beta (1-37) and amyloid-beta (1-39) in the cell, comprising contacting said cell with a compound of formula I, prepared according to methods of the present invention.

As used herein, the term "reducing" or "reduce" refers to the relative decrease in the amount of an amyloid-beta achieved by administering a compound of formula I, prepared according to methods of the present invention, as compared to the amount of that amyloid-beta in the absence of administering a compound of formula I, prepared according to methods of the present invention. By way of example, a reduction of amyloid-beta (1-42) means that the amount of amyloid-beta (1-42) in the presence of a compound of formula I, prepared according to methods of the present invention, is lower than the amount of amyloid-beta (1-42) in the absence of a compound of formula I, prepared according to methods of the present invention.

In still other embodiments, the present invention provides a method for selectively reducing amyloid-beta (1-42) peptide levels in a patient, wherein said method comprises administering to said patient a compound of formula I, prepared according to methods of the present invention, or a pharmaceutically acceptable composition thereof. In certain embodiments, the present invention provides a method for reducing amyloid-beta (1-42) peptide levels in a patient without substantially reducing amyloid-beta (1-40) peptide levels, wherein said method comprises administering to said patient a compound of formula I, prepared according to methods of the present invention, or a pharmaceutically acceptable composition thereof.

In certain embodiments, the present invention provides a method for reducing amyloid-beta (1-42) peptide levels in a patient and increasing at least one of amyloid-beta (1-37) and amyloid-beta (1-39), wherein said method comprises administering to said patient a compound of formula I, prepared according to methods of the present invention, or a pharmaceutically acceptable composition thereof.

The term "increasing" or "increase," as used herein in reference to an amount of an amyloid-beta, refers to the relative rise in the amount of an amyloid-beta achieved by administering a compound of formula I, prepared according to methods of the present invention, (or contacting a cell with a compound of formula I) as compared to the amount of that amyloid-beta in the absence of administering a compound of formula I, prepared according to methods of the present invention, (or contacting a cell with a compound of formula I). By way of example, an increase of amyloid-beta (1-37) means that the amount of amyloid-beta (1-37) in the presence of a compound of formula I, prepared according to methods of the present invention, is higher than the amount of amyloid-beta (1-37) in the absence of a compound of formula I, prepared according to methods of the present invention. For instance, the relative amounts of either of amyloid-beta (1-37) and amyloid-beta (1-39) can be increased either by an increased production of either of amyloid-beta (1-37) and amyloid-beta (1-39) or by a decreased production of longer amyloid-beta peptides, e.g., amyloid-beta (1-40) and/or amyloid-beta (1-42). In addition, it will be appreciated that the term "increasing" or "increase," as used herein in reference to an amount of an amyloid-beta, also refers to the absolute rise in the amount of an amyloid-beta achieved by administering a compound of formula I, prepared according to methods of the present invention. Thus, in certain embodiments, the present invention provides a method for increasing the absolute level of at least one of amyloid-beta (1-37) and amyloid-beta (1-39), wherein said method comprises administering to said patient a compound of formula I, prepared according to methods of the present invention, or a pharmaceutically acceptable composition thereof. In other embodiments, the present invention provides a method for increasing the level of at least one of amyloid-beta (1-37) and amyloid-beta (1-39), wherein the increase is relative to the amount of longer amyloid-beta peptides, e.g., amyloid-beta (1-40) and/or amyloid-beta (1-42), or total amyloid-beta, wherein said method comprises administering to said patient a compound of formula I, prepared according to methods of the present invention, or a pharmaceutically acceptable composition thereof.

One of ordinary skill in the art will appreciate that overall ratio of amyloid-beta peptides is significant where selective reduction of amyloid-beta (1-42) is especially advantageous. In certain embodiments, the present compounds reduce the overall ratio of amyloid-beta (1-42) peptide to amyloid-beta (1-40) peptide. Accordingly, another aspect of the present invention provides a method for reducing the ratio of amyloid-beta (1-42) peptide to amyloid-beta (1-40) peptide in a patient, comprising administering to said patient a compound of formula I, prepared according to methods of the present invention, or a pharmaceutically acceptable composition thereof. In certain embodiments, the ratio of amyloid-beta (1-42) peptide to amyloid-beta (1-40) peptide is reduced from a range of about 0.1 to about 0.4 to a range of about 0.05 to about 0.08.

In other embodiments, the present invention provides a method for reducing the ratio of amyloid-beta (1-42) peptide to amyloid-beta (1-40) peptide in a cell, comprising contacting the cell with a compound of formula I, prepared according to methods of the present invention. In certain embodiments, the ratio of amyloid-beta (1-42) peptide to amyloid-beta (1-40) peptide is reduced from a range of about 0.1 to about 0.4 to a range of about 0.05 to about 0.08.

According to one aspect, the present invention provides a method for treating or lessening the severity of a disorder associated with amyloid-beta (1-42) peptide, wherein said method comprises administering to said patient a compound of formula I, or a pharmaceutically acceptable composition thereof. Such disorders include neurodegenerative disorders such as Alzheimer's disease (familial and sporadic), Parkinson's disease, and Down's syndrome.

Such disorders also include inclusion body myositis (deposition of A-beta in peripheral muscle, resulting in peripheral neuropathy), cerebral amyloid angiopathy (amyloid in the blood vessels in the brain), and mild cognitive impairment.

"High A-beta42" is a measurable condition that precedes symptomatic disease, especially in familial patients, based on plasma, CSF measurements, and/or genetic screening. This concept is analogous to the relationship between elevated cholesterol and heart disease. Thus, another aspect of the present invention provides a method for preventing a disorder associated with elevated amyloid-beta (1-42) peptide, wherein said method comprises administering to said patient a compound of formula I, prepared by methods of the present invention, or a pharmaceutically acceptable composition thereof.

In other embodiments, the present invention provides a method for treating a diseases where A-beta amyloidosis may be an underlying aspect or a co-existing and exacerbating factor, wherein said method comprises administering to said patient a compound of formula I, prepared by methods of the present invention, or a pharmaceutically acceptable composition thereof.

In still other embodiments, the present invention provides a method for treating a disorder in a patient, wherein said method comprises administering to said patient a compound of formula I, or a pharmaceutically acceptable composition thereof, and wherein said disorder is Lewy body dementia (associated with deposition of alpha-synuclein into Lewy bodies in cognitive neurons; a-synuclein is more commonly associated with deposits in motor neurons and the etiology of Parkinson's disease), Parkinson's disease, cataract (where a-beta is aggregating in the eye lens), Tauopathies (e.g. frontotemporal dementia), Huntington's disease, ALS/Lou Gerhig's disease, Type 2 diabetes (IAPP aggregates in pancreatic islets, is similar in size and sequence to A-beta and having type 2 diabetes increases risk of dementia), Transthyretin amyloid disease (TTR, an example of this disease is in heart muscle contributing to cardiomyopathy), prion disease, and Creutzfeldt-Jakob disease (CJD).

In other embodiments, the present invention provides a method for treating or lessening the severity of Alzheimer's disease in a patient, wherein said method comprises administering to said patient a compound of formula I, prepared by methods of the present invention, or a pharmaceutically acceptable composition thereof.

Without wishing to be bound by any particular theory, it is believed that the present compounds are modulators of gamma-secretase which selectively reduce levels of amyloid-beta (1-42). Accordingly, another embodiment of the present invention provides a method of modulating gamma-secretase in a patient, comprising administering to said patient a compound of formula I, prepared according to methods of the present invention, or pharmaceutically acceptable composition thereof. In certain embodiments, the present compounds are inhibitors of gamma-secretase. Said method is useful for treating or lessening the severity of any disorder associated with gamma-secretase. Such disorders include, without limitation, neurodegenerative disorders, e.g. Alzheimer's disease.

The Notch/Delta signaling pathway is highly conserved across species and is widely used during both vertebrate and invertebrate development to regulate cell fate in the developing embryo. See Gaiano and Fishell, "The Role of Notch in Promoting Glial and Neural Stem Cell Fates" *Annu. Rev. Neurosci.* 2002, 25:471-90. Notch interacts with the gamma-secretase complex and has interactions with a variety of other proteins and signaling pathways. Notch1 competes with the amyloid precursor protein for gamma-secretase and activation of the Notch signaling pathway down-regulates PS-1 gene expression. See Lleo et al., "Notch1 Competes with the Amyloid Precursor Protein for γ-Secretase and Down-regulates Presenilin-1 Gene Expression" *Journal of Biological Chemistry* 2003, 48:47370-47375. Notch receptors are processed by gamma-secretase acting in synergy with T cell receptor signaling and thereby sustain peripheral T cell activation. Notch1 can directly regulate Tbx21 through complexes formed on the Tbx21 promoter. See Minter et al., "Inhibitors of γ-secretase block in vivo and in vitro T helper type 1 polarization by preventing Notch upregulation of Tbx21," *Nature Immunology* 2005, 7:680-688. In vitro, gamma-secretase inhibitors extinguished expression of Notch, interferon-gamma and Tbx21 in TH1-polarized CD4+ cells. In vivo, administration of gamma-secretase inhibitors substantially impeded TH1-mediated disease progression in the mouse experimental autoimmune encephalomyelitis model of multiple sclerosis suggesting the possibility of using such compounds to treat TH1-mediated autoimmunity See Id. Inhibition of gamma-secretase can alter lymphopoiesis and intestinal cell differentiation (Wong et al., "Chronic Treatment with the γ-Secretase Inhibitor LY-411,575 Inhibits β-Amyloid Peptide Production and Alters Lymphopoiesis and Intestinal Cell Differentiation" *Journal of Biological Chemistry* 2004, 26:12876-12882), including the induction of goblet cell metaplasia. See Milano et al., "Modulation of Notch Processing by g-Secretase Inhibitors Causes Intestinal Goblet Cell Metaplasia and Induction of Genes Known to Specify Gut Secretory Lineage Differentiation" *Toxicological Sciences* 2004, 82:341-358.

Strategies that can alter amyloid precursor protein ("APP") processing and reduce the production of pathogenic forms of amyloid-beta without affecting Notch processing are highly desirable. Moreover, as described above, the inhibition of gamma-secretase has been shown in vitro and in vivo to inhibit the polarization of Th cells and is therefore useful for treating disorders associated with Th1 cells. Th1 cells are involved in the pathogenesis of a variety of organ-specific autoimmune disorders, Crohn's disease, *Helicobacter pylori*-induced peptic ulcer, acute kidney allograft rejection, and unexplained recurrent abortions, to name a few.

According to one embodiment, the invention relates to a method of inhibiting the formation of Th1 cells in a patient comprising the step of administering to said patient a compound of the present invention, or a composition comprising said compound. In certain embodiments, the present invention provides a method for treating one or more autoimmune disorders, including irritable bowel disorder, Crohn's disease, rheumatoid arthritis, psoriasis, *Helicobacter pylori*-induced peptic ulcer, acute kidney allograft rejection, multiple sclerosis, or systemic lupus erythematosus, wherein said method comprises administering to said patient a compound of formula I, prepared according to methods of the present invention, or a pharmaceutically acceptable composition comprising said compound.

In certain embodiments, the present invention provides a method for modulating and/or inhibiting amyloid-beta peptide production, without affecting Notch processing, in a patient, wherein said method comprises administering to said patient a compound of formula I, prepared according to methods of the present invention, or a pharmaceutically acceptable composition comprising said compound.

In certain embodiments, the present invention provides a method for inhibiting amyloid-beta (1-42) peptide production, without affecting Notch processing, in a patient, wherein said method comprises administering to said patient a compound of formula I, prepared according to methods of the present invention, or a pharmaceutically acceptable composition comprising said compound.

In certain embodiments, the present invention provides a method for reducing amyloid-beta (1-42) peptide levels in a patient and increasing at least one of amyloid-beta (1-37) and amyloid-beta (1-39), without affecting Notch processing, wherein said method comprises administering to said patient a compound of formula I, prepared according to methods of the present invention, or a pharmaceutically acceptable composition thereof.

Accordingly, another aspect of the present invention provides a method for reducing the ratio of amyloid-beta (1-42) peptide to amyloid-beta (1-40) peptide in a patient, without affecting Notch processing, comprising administering to said patient a compound of formula I, prepared according to methods of the present invention, or a pharmaceutically acceptable composition thereof. In certain embodiments, the ratio of amyloid-beta (1-42) peptide to amyloid-beta (1-40) peptide is reduced from a range of about 0.1 to about 0.4 to a range of about 0.05 to about 0.08.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient," as used herein, means an animal, preferably a mammal, and most preferably a human.

EXAMPLES

The following experimentals describe the isolation and/or enrichment of compounds for use in methods of the present invention. The black cohosh extract, utilized in the separation protocol described below, was obtained as a custom order from Boehringer Ingelheim Nutriceuticals. This extract is substantially equivalent to the USP preparation of black cohosh extract, in which about 50% aqueous ethanol is used to extract powdered root and then concentrated to near dryness.

As used herein, the compound numbers recited below correspond to the following compounds:

Compound 1: β-D-Xylopyranoside, (3,12,16,23R,24R,25S,26S)-12-(acetyloxy)-16,23:23,26:24,25-triepoxy-26-hydroxy-9,19-cyclolanostan-3-yl.

Also known as "actein." $C_{37}H_{56}O_{11}$; Mol. Wt.: 676.83; Registry 18642-44-9.

Compound 2: Cimigenol 3-β-D-xylopyranoside; $C_{35}H_{56}O_9$, Mol. Wt.: 620.81; Registry 27994-11-2.

Compound 3: Cimigenol 3-α-L-arabinoside. $C_{35}H_{56}O_9$, Mol. Wt.: 620.81; Registry 256925-92-5.

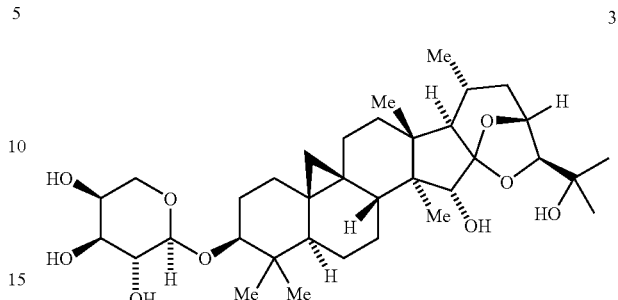

Compound 4: 24-O-Acetylhydroshengmanol 3-β-D-xylopyranoside. $C_{37}H_{60}O_{11}$, Mol. Wt.: 680.87; Registry 78213-32-8.

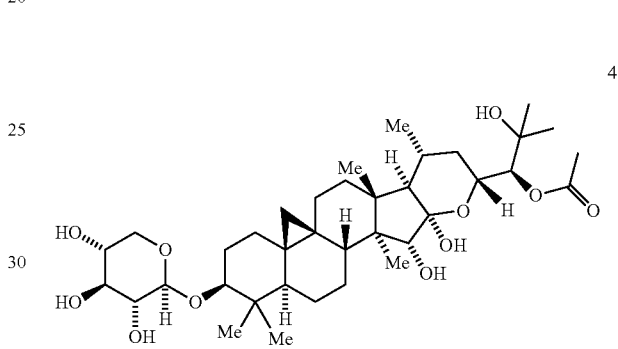

Compound 5: 24-O-Acetylhydroshengmanol 3-α-L-arabinopyranoside. $C_{37}H_{60}O_{11}$, Mol. Wt.: 680.87.

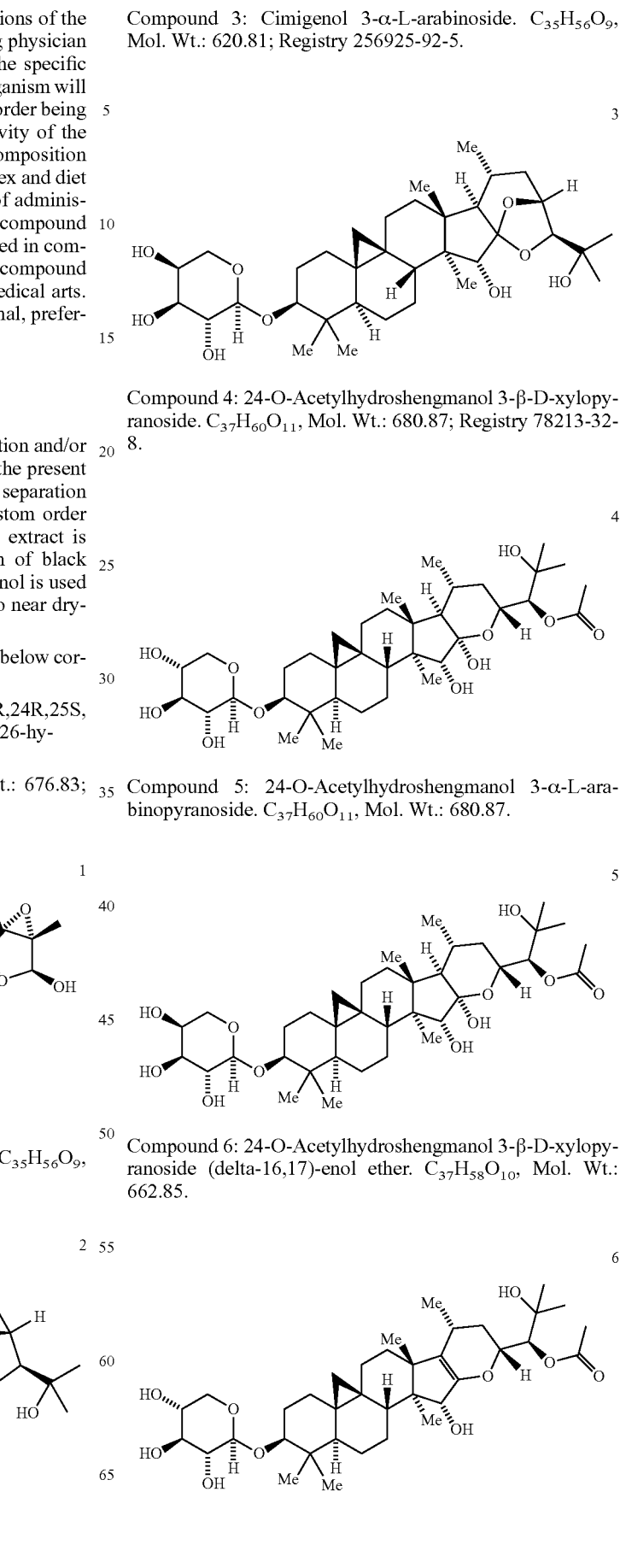

Compound 6: 24-O-Acetylhydroshengmanol 3-β-D-xylopyranoside (delta-16,17)-enol ether. $C_{37}H_{58}O_{10}$, Mol. Wt.: 662.85.

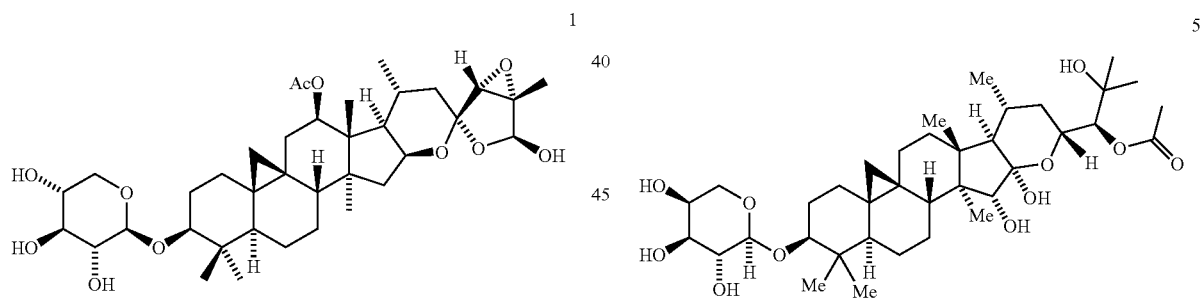

Compound 7: 24-O-Acetylhydroshengmanol 3-α-L-arabinopyranoside (delta-16,17)-enol ether. $C_{37}H_{58}O_{10}$, Mol. Wt.: 662.85.

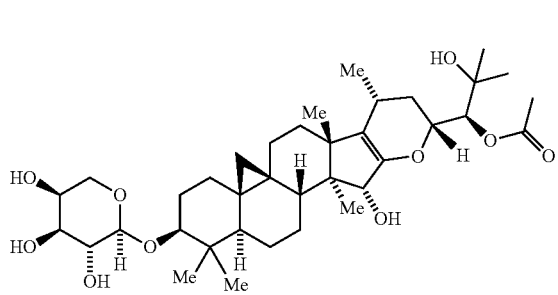

Compound 8: 24-epi-24-O-Acetylhydroshengmanol 3-β-D-xylopyranoside. $C_{37}H_{60}O_{11}$, Mol. Wt.: 680.87.

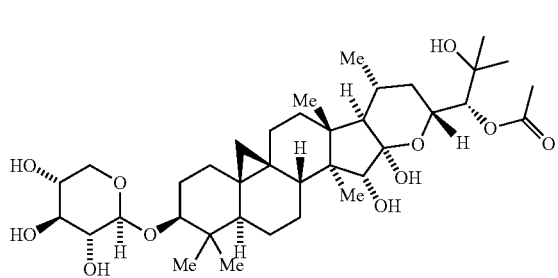

Compound 9: 24-epi-24-O-Acetylhydroshengmanol 3-β-D-xylopyranoside (delta-16,17)-enol ether. $C_{37}H_{58}O_{10}$, Mol. Wt.: 662.85.

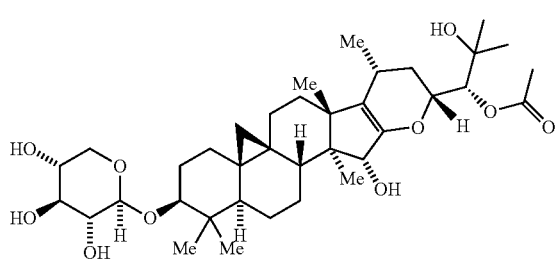

Isolation Protocol 1

Flash Column Chromatography

Black cohosh extract (15.6 g) was suspended in 150 ml of a 4-to-1 (v/v) methanol-water mixture at 25° C. Using a mechanical stirrer, the resulting slurry was vigorously stirred for 30 minutes at this temperature, which resulted in a brown emulsion. To this emulsion, 51 g of silica gel (ICN silica 32-63 60 Å) was added with continued stirring. The mixture was concentrated at 25° C. in vacuo using a rotary evaporator, until a largely homogenous beige-brown powder was obtained. This material was subjected to column chromatography on silica gel (ICN silica 32-63 60 Å) using a 60 cm long glass column with 50 mm inner diameter.

In preparation for the column chromatography silica gel was poured into 500 ml of a 20-to-1 dichloromethane-methanol mixture, and the resulting slurry was poured into the glass column. The silica gel was allowed to settle for 30 minutes, and covered with a 1 cm thick layer of sand. Subsequently, the extract absorbed onto silica was poured into 20-to-1 dichloromethane-methanol mixture, and the resulting slurry was poured onto the sand layer on top of the column. The silica column was then eluted with the following solvent mixtures under a pressure of 0.4 bar (argon):

1.0 ml of dichloromethane-methanol 20-to-1, followed by 770 ml of dichloromethane-methanol 10-to 1, followed by 800 ml of dichloromethane-methanol 7-to-1, followed by 550 ml of dichloromethane-methanol 5-to-1.

Eight 200 ml-fractions (labeled as sat14-0 through sat14-7) were collected, followed by eleven 100-ml fractions (labeled as sat14-8 through sat14-18). All fractions were analyzed by thin-layer chromatography (TLC), using Bakerflex silica plates, eluted with a 5-to-1 dichloromethane-methanol solvent mixture. After development, the silica gel plates were stained with anisaldehyde stain. Based on the results of the TLC analyses, fractions sat14-9 through sat14-12 were evaporated to dryness in vacuo at 25° C., and 10-mg samples of these fractions were analyzed by $^1$H-NMR spectroscopy, using $CD_3OD$ as solvent. Spectra were analyzed with regard to the presence of a broad multiplet at 2.53 ppm, and a 2.2-Hz doublet at 4.86 ppm, because these signals are characteristic for compounds 7 and 6. Additional dqf-COSY spectra of these four samples confirmed that the signals at 2.53 and 4.86 ppm in fact belong to compounds 7 and 6. From the $^1$H-NMR spectra of fraction sat14-10 it was concluded that this sample contained the highest concentration of compounds 7 and 6, while slightly smaller amounts of these compounds could be detected in fraction sat14-9. Fraction sat14-11 appeared to contain traces of 7 and 6, whereas these compounds could not be detected in fraction sat14-12. Based on these results, fraction sat14-10 was chosen for further purification via HPLC. Alternatively, fraction sat14-9 could be used, to obtain additional amounts of compounds 4 through 7 as needed.

The major component of fraction sat14-10 was actein (1) (JNP 2002, 65, 601-605), which crystallized from a methanolic solution of this fraction. Pure actein was obtained through recrystallization. Major components of fraction sat14-11 were cimigenol beta-D-xylopyranoside (2) and cimigenol alpha-L-arabinoside (3), which crystallized from this fraction as a mixture of roughly 2:1 (JNP 2000, 65, 905-910 and 1391-1397).

Reversed-Phase HPLC Fractionation on C-18 Column

Fraction sat14-10 was dissolved in 3.5 ml of methanol. This solution was fractionated by HPLC using a SUPELCO Discovery RP-18 column (25 cm length, 10 mm inner diameter), and an AGILENT 1100 series HPLC system, including auto-injector and a diode array detector used for detection of wavelength from 190-400 nm. A solvent gradient was employed, starting with 30% (v/v) water in methanol for the first two minutes, followed by a linear decrease of water content reaching 100% methanol at 20 minutes. After 2 minutes at 100% methanol, water content was increased to 30% and maintained at that concentration for another 8 minutes. For separation of the entire sample sat14-10, 100 injections of 35 µl each were required. Nine fractions were collected, which were labeled sat15-1 through sat15-9. Compounds 4 through 7 were eluted in fractions sat15-1, 15-2, 15-4 and 15-5:

Reversed-Phase HPLC Fractionation on $C_{1-8}$ Column for the Isolation of 6, 4, and 9

Fraction sat15-5 was dissolved in 1.5 ml of methanol. This solution was fractionated by HPLC using a SUPELCO supelcosil LC-8 column (25 cm length, 10 mm inner diameter), and the AGILENT 1100 series HPLC system described above. A solvent gradient was employed, starting with 40% (v/v) water in methanol for the first two minutes, followed by a linear decrease of water content reaching 100% methanol at 20 minutes. After 2 min at 100% methanol, water content was increased to 40% and maintained at that concentration for another 8 minutes. For separation of the entire sample sat15-5, 50 injections of 30 µl each were required. Five fractions were collected, which were labeled sat16-1 through sat16-5. Compound 6 was eluted in fraction sat16-3, whereas compound 4 eluted in fraction sat16-1. A small amount of pure 9 was obtained in fraction sat15-5.

Reversed-Phase HPLC Fractionation on C-8 Column for the Isolation of 8

Fraction sat15-8 was dissolved in 0.65 ml of methanol. This solution was fractionated by HPLC using a SUPELCO supelcosil LC-8 column (25 cm length, 10 mm inner diameter), and the AGILENT 1100 series HPLC system described above. A solvent gradient was employed, starting with 40% (v/v) water in methanol for the first two minutes, followed by a linear decrease of water content reaching 100% methanol at 20 minutes. After 2 minutes at 100% methanol, water content was increased to 40% and maintained at that concentration for another 8 minutes. Seven fractions were collected, which were labeled sat18-1 through sat18-7. Compound 8 was eluted in fraction sat18-6. NMR-spectroscopic analyses including NOESY spectra showed that in methanolic solution compound 8 interconverts with the corresponding ketone. Dilute methanolic solutions contain about 4% ketone and 96% of the hemiacetal form.

Reversed-Phase HPLC Fractionation on C-8 Column for the Isolation of 7 and 5

Fraction sat15-2 was dissolved in 0.5 ml of methanol. This solution was fractionated by HPLC using a SUPELCO supelcosil LC-8 column (25 cm length, 10 mm inner diameter), and the AGILENT 1100 series HPLC system described above. A solvent gradient was employed, starting with 40% (v/v) water in methanol for the first two minutes, followed by a linear decrease of water content reaching 100% methanol at 20 minutes. After 2 minutes at 100% methanol, water content was increased to 40% and maintained at that concentration for another 8 minutes. Five fractions were collected, which were labeled sat19-3 through sat19-7. Pure compound 7 was obtained in fraction sat19-7, whereas pure compound 5 was obtained in fraction sat19-5.

Isolation Protocol 2

An alternative isolation/purification protocol is set forth below for isolating compound 6. One of ordinary skill in the art will recognize that while isolating compound 6, other compounds of the present invention are enriched and/or isolated by this process.

This purification protocol utilized the following equipment:
(a) Hitachi HPLC system with diode array detector (DAD)
(b) Nova Prep™ 8000 SEMI-Preparative HPLC with Remote PC Controller using LC ReSponder™ Application Software
(c) Hitachi UV Detector L-7400
(d) Sedex 55 evaporative light scattering (ELSD) detector
(e) 75L Biotage silica column (KP-Sil; P/N FKO-1107-19073; Lot 027075L)
(f) 75L Biotage C18 column (Bakerbond, 40µ)
(g) 75S Biotage C18 column (Vydac, 40µ)
(h) Analytical HPLC column: Phenomenex Luna C18, 3µ, 4.6×100 mm
(i) Semi-Preparative HPLC column: Phenomenex Luna C8 HPLC column, 20×250 mm
(j) Semi-Preparative HPLC column: YMC AQ C18 HPLC column, 21.2×250 mm; and
(k) Preparative HPLC column: ES Industries C18 Preparative HPLC column; 5×25 cm.

The analytical method utilized to determine the purity of compound 6 is as follows:
Column: Phenomenex Luna C18, 3µ, 4.6×100 mm
Mobile Phase Isocratic elution with A. 35% Acetonitrile; B. 30% Nanopure water containing 0.05% Acetic Acid; and C. 35% MeOH
Flow Rate: 1 mL/min
Detection: 205, 230 nm, DAD; and ELSD
Run Time: 8 min
Column Temperature: 32° C.
This method was used for the analysis of the extract, fractions, and the final product. Compound 6 elutes at about 5.5 minutes under these conditions.

50 g of crude black cohosh extract ("BCE") was fractionated on a Biotage Silica cartridge (7.5×30 cm). After loading, the cartridge was eluted with 5% MeOH/DCM (10 L) and 10% MeOH/DCM (5 L) and 500 ml fractions were collected. The flow rate was 150-200 ml/min. The HPLC (UV at 230 nm) revealed the compound 6 was present in fractions 23 (2.6 g) and 24 (2.3 g). The fraction 23 (F23) was selected for further purification on a semi-prep C8 column.

Ten runs were performed to get approximately 10 mg of compound 6. 50 mg of F23 in 0.3 ml of MeOH was loaded onto a Phenomenex Luna C-8 (21.2×250 mm, 10µ, 100 A) semi-prep column. The column was eluted at a flow rate of 9.9 mL/min with 70% MeOH in $H_2O$ with UV monitoring at 205 nm. The peaks eluting at 35 min and 38 min as shown in semi-prep HPLC trace were separately collected.

The fractions collected for the peak at 35 min from the 10 runs were pooled and solvents evaporated at ambient temperature. The resulting solids were dried on a lyophilizer to yield 10.3 mg of compound 6 (2609-165-7). The HPLC of the product 2609-165-7 revealed a polar impurity peak (11.3%) with retention time (RT) at 4.5 min, although the HPLC of individual fractions showed only one major peak. Apparently compound 6 converted slowly during the process to a more polar compound. It was found that the more polar compound was the deacetyl derivative of compound 6 as evident from SSI-MS which showed an intense $[M+Na]^+$ peak at m/z 643 and proton NMR of the isolated impurity at 4.5 min in which the singlet for the acetyl methyl was absent.

A few stability experiments with compound 6 indicated that deacetylation occurred in MeOH solution which is slightly basic. However, it was stable in slightly acidic solution. Therefore, 2609-165-7 was re-processed on the Luna C8 column using 70% MeOH/30% water containing 0.05% AcOH as eluent to give 3.4 mg of compound 6 (2609-172-11).

In another process, 250 g of black cohosh extract (BCE) was stirred with 1250 mL of MeOH for 1 hr at room temperature in a beaker. Not all the solids dissolved but HPLC analysis of a filtrate indicated that all compound 6 in the starting extract dissolved (~250 mg). Nonetheless the unfiltered mixture was added to 750 g of silica gel (ICN, 60-200 g) in a 5 L round bottom flask. The MeOH was removed on the rotovap with the aid of vacuum to a dry powder weighing 1100 g with 9% residual MeOH.

The BCE dried on silica preparation was divided into four parts of approximately 270 g each. The mixture was loaded into the SIM (sample injection module) and first washed with 500-600 mL of methylene chloride to remove non-polars and residual MeOH. The SIM was connected to the 75L silica column (KP-Sil; P/N FKO-1107-19073; Lot 027075L; 7.5×25 cm or 1750 mL). The main column was radial compressed at 60 psi. The system was eluted with acetone at a flow rate of amount 100 mL/min, and 500-1000 mL fractions were collected. After the elution of compound 6 the column was washed with 1.0 L of MeOH and re-equilibrated with 2 L of acetone. Compound 6 was observed to elute primarily in Fraction 3 (1000 mL) after approximately 900-1000 mL of acetone had eluted from the column in Fractions 1 and 2. The first four runs yielded approximately 224 mg of compound 6. A second batch of starting material for the silica Biotage was prepared from 100 g of BCE and 500 mL of MeOH and 300 g of silica. Two additional Biotage runs (5 and 6) were done similar to the first four with this starting material yielding another 93 mg of compound 6. The product pools from the six runs were combined and evaporated to a dry solid under reduced pressure.

The dried solids (90 g) from the silica Biotage were dissolved in 720 mL of MeOH and 480 mL of $H_2O$ was added slowly with stirring. Some dark tar-like solids precipitated out and were removed on a filter. The cloudy filtrate was loaded on a 75 L (7.5×25 cm) Bakerbond 60 Å, 40µ Biotage C18 column. After the loading, which tested negative from compound 6, the column was washed with 5 L of 60% (v/v) MeOH/$H_2O$ followed by 4 L of 70% MeOH/$H_2O$, and then eluted compound 6 using 4 L of 80% MeOH/$H_2O$. After the elution the column was washed with 2 L of MeOH. The flow rate was about 60 mL/min throughout and the MeOH/$H_2O$ mobile phases contained 0.05% acetic acid in order to prevent degradation of compound 6. The product pool (4 L) was concentrated under reduced pressure until essentially all the MeOH was removed and the resulting precipitated solids collected on a Buchner funnel and dried with the aid of high vacuum at room temperature.

The tar-like solids removed via filtration from the first large-scale C18 feed preparation and containing about 32 mg of compound 6 were dissolved in 2 L of MeOH wash from the large-scale experiment and which contained about 22 mg of Compound 6. The mixture was evaporated to 1 L and mixed with 0.67 L of water. Some tar-like solids precipitated out which were collected on a filter, dissolved in 200 mL of MeOH, and mixed with 134 mL of water. This mixture was also filtered to remove a small amount of tar and the filtrate combined with the first filtrate and loaded on a 75S (7.5×9.0 cm; 400 mL) Vydac 300 Å, 40µ Biotage C18 column. The column was washed with 1 L of 60% MeOH/$H_2O$ and 2 L of 70% MeOH/$H_2O$, and eluted with 1 L of 80% MeOH/$H_2O$ (mobile phases also contained 0.05% acetic acid). The product pool was evaporated and the solids collected by filtration similar to the large-scale Biotage experiment.

The first product pool (16.69 g) from the C18 Biotage column was mixed with 70 mL of MeOH. The mixture was sonicated, and the precipitate was removed by filtration. The filtrate was chromatographed (five runs, 14 mL each) on an ES Industries Chromegabond WR C18 column at flow rate of 177 mL/min using 70% MeOH/30% water containing 0.05% AcOH as eluent. The fractions from the 6-14 minutes of each run were combined, and evaporated to remove MeOH. The precipitate after removal of MeOH was collected by centrifugation, and dried on a lyophilizer to give 6.6 g dried solids 2609-173-16 (compound 6, 3.2%).

The second product pool (4.3 g) from the C18 Biotage column was processed in similar manner to give 2.0 g dried solids 2609-173-27 (compound 6, 3.06%). 2609-173-16 and 2609-176-27 were combined to yield 8.6 g of 2609-174-6.

2609-174-6 (400 mg) was dissolved in 1.3 mL of MeOH containing 0.1% AcOH. The solution was loaded onto a Phenomenex Luna C8 column which was eluted at flow rate of 24 mL/min with 68% MeOH/32% water containing 0.05% AcOH.

Based on analytical HPLC, the fractions from the 15.8 to 19.8 minute of each run (total 22 runs) were combined, evaporated to remove MeOH, and lyophilized to dryness to give 2609-174-28 (1.4 g containing 12.6% of compound 6). 2609-174-28 was used for the final isolation of compound 6 on a YMC-AQ C18 column. A total of 28 runs were performed.

2609-174-28 (50 mg) was dissolved in 0.25 mL of MeOH containing 0.1% AcOH. The solution was injected into the YMC AQ C18 column. The column was eluted at 9.9 mL/min with 70% MeOH/30% water containing 0.05% AcOH. Based on analytical HPLC profiles, selected fractions, typically between 48.4-50.4 minute, from the 28 runs were pooled, evaporated, and lyophilized to yield compound 6 (2609-176-30, 85 mg).

The fractions that were collected immediately before 48.4 min and contained mainly compound 6 were also combined, and dried to give 2609-176-35 (50 mg). 2609-176-35 was re-processed (3 runs) using the same column and mobile phase to yield another lot of compound 6 which was combined with 2609-176-30 to give 102 mg of product (2609-177-10) with ~95% chromatography purity.

Dehydration Reaction

Using the conversion of compound 4 to compound 6 to exemplify, the following procedures describe the conversion of a compound of formula II to a compound of formula I.

The conversion of compound 4 to compound 6 was monitored by the following HPLC methods:
Method 1: A 4.6×100 mm, 3µ Luna(2) C18 column from Phenomenex (P/N 00D-4251-E0) was used with a mobile phase of 35/30/35 MeCN/$H_2O$/MeOH (isocratic) for 8 min. Detection was via ELSD and UV at 205 and 230 nm.
Method 2: A 4.6×100 mm, 3µ Luna(2) C18 column from Phenomenex (P/N 00D-4251-E0) was used with a mobile phase of 75/25 MeOH/$H_2O$ (Method 2) at 1 mL/min. Detection was via ELSD and UV at 205 and 230 nm. The Method 2 was used primarily for the black cohosh extract (BCE) experiments.

Conversion of Purified Compound 4 to Compound 6 with TFA: 1. 9 mg of purified compound 4 (2631-61-9; 92% purity) was sonicated with 2 mL of MeOH (w/0.1% HOAc) then treated with 0.040 mL of TFA (4%) and after 1 hr the reaction was quenched with 6 N $NH_4OH$ to pH 6.

A second conversion experiment was done by dissolving 10 mg of compound 4 (2631-61-15; 83% purity) in 3 mL of MeOH and adding 0.15 mL (5%) TFA. After sitting at room temperature for 40 min, the reaction mixture was quenched with 6 N $NH_4OH$ to pH 6. The HPLC analysis (ELSD) indicated that most of compound 4 had converted to compound 6. The HPLC analysis (Method 1) of the starting material indicated compound 4 was 2.7 mg/ml before the reaction and 0.5 mg/ml after and that compound 6 was 0.84 mg/ml after the conversion.

Conversion of Crude Compound 4 to Compound 6:
Step A: Preparation of Methanolic BCE: 1.00 g of black cohosh extract (BCE) was sonicated at room temperature for 1 hr with 15.0 mL of methanol containing 0.1% acetic acid (HOAc). The mixture was filtered through a 0.45 micron PTFE membrane filter into a vial.
Step B(1): Acid-Treatment of Methanol BCE: (Experiment 1) 1.0 mL of the methanolic BCE was treated with 0.05 mL of TFA in an HPLC vial. The untreated control and the treated sample were analyzed by HPLC after 0.5 hr, 2.5 hr, 3.5 hr, and 2.5 days. Treatment of the methanolic extract of BCE with 5% TFA appeared to completely convert compound 4 to compound 6 in about 3.5 hr.

Step B(2): Acid-Treatment of Methanol BCE: (Experiment 2) Fresh BCE (1 g in 15 mL of MeOH) was used in a second series of experiments in which compound 4 and compound 6 were quantitated against pure compound 4 and compound 6 standards. 1.0 mL of the BCE methanolic solution was treated with 30, 50, and 100 μL of TFA in a HPLC vial and the samples analyzed over a period of 6 hr by the HPLC Method 1. Compound 6 was quantitated at 230 nm and Peak 2 was quantitated using both ELSD and UV at 205 nm. Analysis of the untreated control indicated that compound 6 in the BCE was 0.135%, while compound 4 was a major component of the extract and was found to be 2.49% using ELSD and 1.95% using UV 205 nm. The data indicated that the cleanest conversion with the highest recovery of compound 6 took place in the sample treated with 3% TFA for a period of 2-2.5 hr. In this sample compound 6's concentration in the acid-treated extract increased from 0.090 mg/mL to 0.64 mg/mL (7.1× or 611%) while the assay for compound 4 indicated that it decreased from 1.30 mg/mL to 0.2 mg/mL (85% loss using UV $_{205}$). The two experiments indicated that the acid treatment increased the amount of Compound 3 in the methanolic BCE by 7-8 fold.

Biological Assays

A. Assay to Determine the Ability of a Compound of the Present Invention to Inhibit Aβ-42

Compounds of the present invention, and extracts comprising said compounds, may be assayed as inhibitors of amyloid-beta (1-42) peptide in vitro or in vivo. Such assay methods are described in detail in U.S. Pat. No. 6,649,196, the entirety of which is hereby incorporated herein by reference.

Compounds of the present invention were found to selectively lower amyloid-beta (1-42) peptide according to the cell-based assay performed in substantially the same manner as described in U.S. Pat. No. 6,649,196.

B. Assay to Determine Ability of a Compound of Formula I to Affect the Ratio of Total Aβ

Compounds of the present invention were assayed to determine their effect on the total ration of amyloid-β (1-42) peptide in vitro using an assay protocol substantially similar to that described by Wang et al., *J. Biol. Chem.* 1996, 50:31894-31902, The Profile of Soluble Amyloid β Protein in Cultured Cell Media, the entirety of which is hereby incorporated herein by reference. This assay quantifies amyloid-β protein using immunoprecipitation and mass spectrometry (IP-MS). Using compound 6 to exemplify, it was found that this compound reduced amyloid-β (1-42) peptide, while increasing amyloid-β (1-37) peptide and amyloid-β (1-39) peptide.

Compound 6 was also assayed according to the method described in Wang et al., in 7W cells (APP$_{wt}$) and 7PA2 cells (APP$_{V717F}$). The APP$_{717}$ mutations increase the relative amount of amyloid-β (1-42) peptide. In this assay, it was shown that compound 6 reduces amyloid-β (1-42) peptide while increasing amyloid-β (1-39) peptide.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

I claim:
1. A method for preparing a compound of formula I:

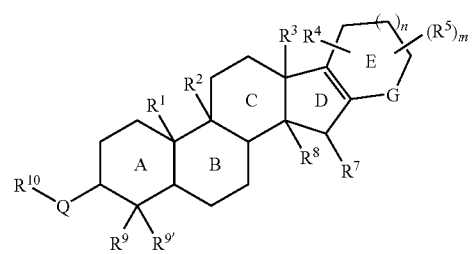

or a pharmaceutically acceptable salt thereof, wherein:
each of Ring A, Ring B, Ring C, Ring D, and Ring E is independently saturated, partially unsaturated or aromatic;
G is S, $CH_2$, NR, or O;
$R^1$ and $R^2$ are each independently halogen, R, OR, a suitably protected hydroxyl group, SR, a suitably protected thiol group, $N(R)_2$, or a suitably protected amino group, or $R^1$ and $R^2$ are taken together to form a 3-7 membered saturated, partially unsaturated, or aryl ring having 0-2 heteroatoms independently selected from nitrogen, oxygen, or sulfur;
each R is independently hydrogen, an optionally substituted $C_{1-6}$ aliphatic group, or an optionally substituted 3-8 membered saturated, partially unsaturated, or aryl ring having 0-4 heteroatoms independently selected from nitrogen, oxygen, or sulfur, wherein:
two R on the same nitrogen atom are optionally taken together with said nitrogen atom to form a 3-8 membered saturated, partially unsaturated, or aryl ring having 1-4 heteroatoms independently selected from nitrogen, oxygen, or sulfur;
n is 0-2;
$R^3$, $R^4$, $R^7$, and $R^8$ are each independently selected from halogen, R, OR, a suitably protected hydroxyl group, SR, a suitably protected thiol group, $SO_2R$, $OSO_2R$, $N(R)_2$, a suitably protected amino group, NR(CO)R, NR(CO)(CO)R, NR(CO)N(R)$_2$, NR(CO)OR, (CO)OR, O(CO)R, (CO)N(R)$_2$, or O(CO)N(R)$_2$;
m is 0-2;
$R^5$ is T-C(R')$_3$, T-C(R')$_2$C(R")$_3$, R, OR, a suitably protected hydroxyl group, SR, a suitably protected thiol group, $SO_2R$, $OSO_2R$, $N(R)_2$, a suitably protected amino group, NR(CO)R, NR(CO)(CO)R, NR(CO)N(R)$_2$, NR(CO)OR, (CO)OR, O(CO)R, (CO)N(R)$_2$, or O(CO)N(R)$_2$, or:
each T is independently a valence bond or an optionally substituted straight or branched, saturated or unsaturated, $C_{1-6}$ alkylidene chain wherein up to two methylene units of T are optionally and independently replaced by —O—, —N(R)—, —S—, —C(O)—, —S(O)—, or —S(O)$_2$—;
each R' and R" is independently selected from R, OR, SR, $SO_2R$, $OSO_2R$, $N(R)_2$, NR(CO)R, NR(CO)(CO)R, NR(CO)N(R)$_2$, NR(CO)OR, (CO)OR, O(CO)R, (CO)N(R)$_2$, or O(CO)N(R)$_2$;
$R^9$ and $R^{9'}$ are each independently selected from halogen, R, OR, SR, or N(R)$_2$, or $R^9$ and $R^{9'}$ are taken together to form a 3-7 membered saturated, partially unsaturated, or aryl ring having 0-2 heteroatoms independently selected from nitrogen, oxygen, or sulfur;

Q is a valence bond or an optionally substituted straight or branched, saturated or unsaturated, $C_{1-6}$ alkylidene chain wherein up to two methylene units of Q are optionally and independently replaced by —O—, —N(R)—, —S—, —C(O)—, —S(O)—, or —S(O)$_2$—; and $R^{10}$ is R, a suitably protected hydroxyl group, a suitably protected thiol group, a suitably protected amino group, an optionally substituted 3-8 membered saturated, partially unsaturated, or aryl monocyclic ring having 0-4 heteroatoms independently selected from nitrogen, oxygen, or sulfur, an optionally substituted 8-10 membered saturated, partially unsaturated, or aryl bicyclic ring having 0-4 heteroatoms independently selected from nitrogen, oxygen, or sulfur, a detectable moiety selected from the group consisting of radioisotopes, mass-tags, fluorescent labels, biotin, and antigen labels, a polymer residue selected from the group consisting of poly(alkylene oxides), a peptide, or a sugar-containing or sugar-like moiety selected from the group consisting of cyclic and acyclic cyclitols, glycosides, arabinopyranoside, xylopyranoside, or erythritol, comprising the steps of:

(a) providing a compound of formula II:

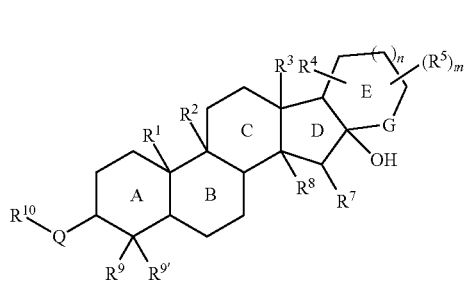

II and (b) converting the compound of formula II to the compound of formula I, where the conversion is achieved by intramolecular dehydration reaction.

2. The method according to claim 1, wherein the dehydration is performed in the presence of a suitable acid.

3. The method according to claim 2, wherein the suitable acid is a Brønsted acid.

4. The method according to claim 3, wherein the Brønsted acid is a hydrogen halide, a carboxylic acid, a sulfonic acid, or a phosphoric acid.

5. The method according to claim 4, optionally performed in the presence of a suitable solvent.

6. The method according to claim 5, wherein the suitable solvent is a protic solvent, a halogenated hydrocarbon, an ether, an ester, an aromatic hydrocarbon, a polar or a nonpolar aprotic solvent, or any mixtures thereof.

7. The method according to claim 1, wherein the compound of formula I is a compound of formula I-a:

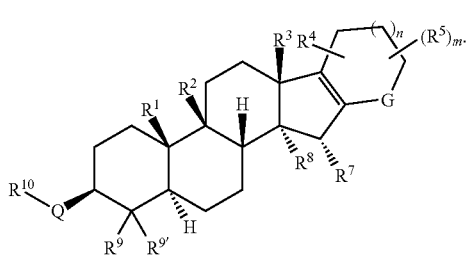

I-a

8. The method according to claim 1, wherein the compound of formula I is a compound of formula I-b:

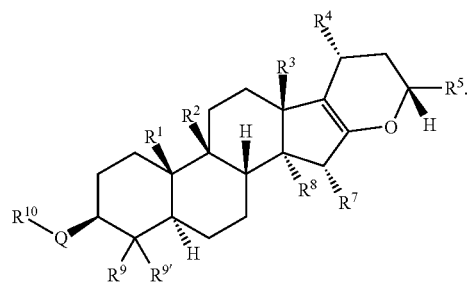

I-b

9. The method according to claim 1, wherein the compound of formula I is a compound of formula I-c:

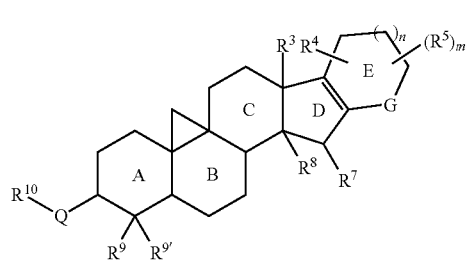

I-c

10. A method for preparing a compound of formula I-i:

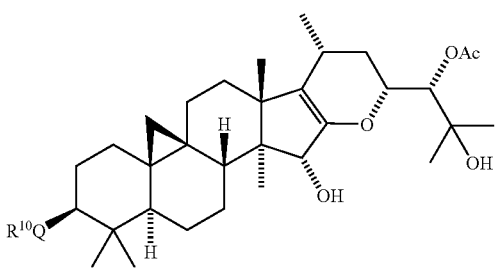

I-i or a pharmaceutically acceptable salt thereof, wherein:

Q is a valence bond or an optionally substituted straight or branched, saturated or unsaturated, $C_{1-6}$ alkylidene chain wherein up to two methylene units of Q are optionally and independently replaced by —O—, —N(R)—, —S—, —C(O)—, —S(O)—, or —S(O)$_2$—;

$R^{10}$ is R, a suitably protected hydroxyl group, a suitably protected thiol group, a suitably protected amino group, an optionally substituted 3-8 membered saturated, partially unsaturated, or aryl monocyclic ring having 0-4 heteroatoms independently selected from nitrogen, oxygen, or sulfur, an optionally substituted 8-10 membered saturated, partially unsaturated, or aryl bicyclic ring having 0-4 heteroatoms independently selected from nitrogen, oxygen, or sulfur, a detectable moiety selected from the group consisting of radioisotopes, mass-tags, fluorescent labels, biotin, and antigen labels, a polymer residue selected from the group consisting of poly(alkylene oxides), a peptide, or a sugar-containing or sugar-like moiety selected from the group consisting of cyclic and acyclic cyclitols, glycosides, arabinopyranoside, xylopyranoside, or erythritol;

R is hydrogen, an optionally substituted $C_{1-6}$ aliphatic group, or an optionally substituted 3-8 membered saturated, partially unsaturated, or aryl ring having 0-4 heteroatoms independently selected from nitrogen, oxygen, or sulfur, wherein:

two R on the same nitrogen atom are optionally taken together with said nitrogen atom to form a 3-8 membered saturated, partially unsaturated, or aryl ring having 1-4 heteroatoms independently selected from nitrogen, oxygen, or sulfur, comprising the steps of:

(a) providing a compound of formula I-ii:

I-ii and (b) converting compound I-ii to compound I-i, where the conversion is achieved by intramolecular dehydration reaction.

11. A method for preparing a compound of formula I-iii:

I-iii or a pharmaceutically acceptable salt thereof, wherein:

Q is a valence bond or an optionally substituted straight or branched, saturated or unsaturated, $C_{1-6}$ alkylidene chain wherein up to two methylene units of Q are optionally and independently replaced by —O—, —N(R)—, —S—, —C(O)—, —S(O)—, or —S(O)$_2$—;

$R^{10}$ is R, a suitably protected hydroxyl group, a suitably protected thiol group, a suitably protected amino group, an optionally substituted 3-8 membered saturated, partially unsaturated, or aryl monocyclic ring having 0-4 heteroatoms independently selected from nitrogen, oxygen, or sulfur, an optionally substituted 8-10 membered saturated, partially unsaturated, or aryl bicyclic ring having 0-4 heteroatoms independently selected from nitrogen, oxygen, or sulfur, a detectable moiety, selected from the group consisting of radioisotopes, mass-tags, fluorescent labels, biotin, and antigen labels, a polymer residue selected from the group consisting of poly(alkylene oxides), a peptide, or a sugar-containing or sugar-like moiety selected from the group consisting of cyclic and acyclic cyclitols, glycosides, arabinopyranoside, xylopyranoside, or erythritol; and R is hydrogen, an optionally substituted $C_{1-6}$ aliphatic group, or an optionally substituted 3-8 membered saturated, partially unsaturated, or aryl ring having 0-4 heteroatoms independently selected from nitrogen, oxygen, or sulfur, wherein:

two R on the same nitrogen atom are optionally taken together with said nitrogen atom to form a 3-8 membered saturated, partially unsaturated, or aryl ring having 1-4 heteroatoms independently selected from nitrogen, oxygen, or sulfur, comprising the steps of:

(a) providing a compound of formula I-iv:

I-iv and (b) converting compound I-iv to compound I-iii, where the conversion is achieved by intramolecular dehydration reaction.

12. The method according to claim 1, wherein: G is O.

13. The method according to claim 1, wherein:

$R^5$ is T-C(R')$_3$ or T-C(R')$_2$C(R")$_3$;

each T is independently a valence bond or a straight or branched $C_{1-4}$ alkylidene chain wherein one methylene unit of T is optionally replaced by —O—, —N(R)—, or —S—; and each R' and R" is independently R, OR, OC(O)R, SR, or N(R)$_2$.

14. The method according to claim 13, wherein:

Q is a an optionally substituted straight or branched, saturated or unsaturated, $C_{1-2}$ alkylidene chain wherein up to one methylene unit of Q is optionally replaced by —O—, —N(R)—, or —S—; and $R^{10}$ is a glycoside.

15. The method according to claim 14, wherein Q is —O— and $R^{10}$ is an arabinopyranoside or a xylopyranoside.

* * * * *